(12) United States Patent
Holdcroft et al.

(10) Patent No.: US 11,299,464 B2
(45) Date of Patent: Apr. 12, 2022

(54) STABLE POLY(IMIDAZOLIUM) HYDROXIDES

(71) Applicant: Simon Fraser University, Burnaby (CA)

(72) Inventors: Steven Holdcroft, Pitt Meadows (CA); Jiantao Fan, Burnaby (CA); Andrew Wright, Mountain View, CA (US); Benjamin Britton, Vancouver (CA); Thomas Weissbach, Burnaby (CA); Timothy James Peckham, Vancouver (CA); Jonathan William Ward, Burnaby (CA)

(73) Assignee: Simon Fraser University, Burnaby (CA)

( * ) Notice: Subject to any disclaimer, the term of this patent is extended or adjusted under 35 U.S.C. 154(b) by 115 days.

(21) Appl. No.: 16/321,414

(22) PCT Filed: Jul. 29, 2017

(86) PCT No.: PCT/US2017/044554
§ 371 (c)(1),
(2) Date: Jan. 28, 2019

(87) PCT Pub. No.: WO2018/023097
PCT Pub. Date: Feb. 1, 2018

(65) Prior Publication Data
US 2019/0382353 A1 Dec. 19, 2019

Related U.S. Application Data

(60) Provisional application No. 62/368,667, filed on Jul. 29, 2016.

(51) Int. Cl.
*C07D 233/64* (2006.01)
*A61P 31/00* (2006.01)

(52) U.S. Cl.
CPC ............ *C07D 233/64* (2013.01); *A61P 31/00* (2018.01)

(58) Field of Classification Search
CPC .............................. C07D 233/64; A61P 31/00
USPC ....................................................... 514/396
See application file for complete search history.

(56) References Cited

U.S. PATENT DOCUMENTS

| 3,255,078 | A | 6/1966 | Heinroth et al. |
| 7,301,002 | B1 | 11/2007 | Cornelius et al. |
| 8,110,636 | B1 | 2/2012 | Fujimoto et al. |
| 9,509,008 | B2 | 11/2016 | Kim et al. |
| 2003/0099838 | A1 | 5/2003 | Cho et al. |
| 2006/0110632 | A1 | 5/2006 | Hong et al. |
| 2009/0026544 | A1 | 1/2009 | Uno et al. |
| 2012/0186446 | A1 | 7/2012 | Bara et al. |
| 2012/0256296 | A1 | 10/2012 | Wei et al. |
| 2015/0073063 | A1 | 3/2015 | Thomas et al. |

FOREIGN PATENT DOCUMENTS

| CA | 2866742 | A1 | 10/2013 | |
| CA | 2933312 | A1 | 9/2016 | |
| JP | 2009-087687 | A | 4/2009 | |
| JP | 2012-128142 | A | 7/2012 | |
| KR | 2012-0115848 | A | 10/2012 | |
| WO | 2009/134227 | A1 | 11/2009 | |
| WO | 2013/149328 | A1 | 10/2013 | |
| WO | WO-2013149328 | A1 * | 10/2013 | .............. B01J 41/13 |
| WO | 2014/012188 | A1 | 1/2014 | |
| WO | 2015/153959 | A2 | 10/2015 | |
| WO | 2015/157848 | A1 | 10/2015 | |

OTHER PUBLICATIONS

Andrew Wright et al. Hydroxide-Stable Ionenes (Year: 2014).*
Hai ling et al Hydroxide Degradation Pathways for Imidazolium Cations:A DFT Study (Year: 2014).*
International Search Report and Written Opinion dated Jul. 16. 2013 issued in corresponding International Application No. PCT/CA2013/000323, filed Apr. 4, 2013, 7 pages.
Pu, H., et al., "Synthesis and Characterization of Fluorine-Containing Polybenzimidazole for Proton Conducting Membranes in Fuel Cells," Journal of Polymer Science: Part A: Polymer Chemistry 48(10):2115-2122, May 2010.
Takagi, K., et al., "Synthesis of Imidazole-Containing Conjugated Polymers Bearing Phenol Unit as Side Group and Excited State Intramolecular Proton Transfer-Mediated Fluorescence," Journal of Polymer Science: Part A: Polymer Chemistry 47(18):4822-4829, Sep. 2009.
Wright, A., et al., "Hydroxide-Stable Ionenes," ACS Macro Letters, vol. 3, No. 5 444-447, May 20, 2014.
Zimmerman, T., et al., "Ring Transformations of Heterocyclic Compounds. XIV [1], Ring Transformations of Pyrylium and Thiopyrylium Salts with Anhydro-bases Derived from 1H-Benzimidazolium and Benzothiazolium Salts: An easy Access to 2-(2,4,6-triarylphenyl) 1H-Benzimidazolium and Benzothiazolium Derivatives," J. Heterocycl. Chem, vol. 33, 1717-1721, 1996.
Williams, T., et al. "Mechanistic Elucidation of the Arylation of Non-Spectator N-Heterocyclic Carbenes at Copper Using a Combined Experimental and Computational Approach," Organometallics, vol. 34, No. 14, 3497-3507, 2015.
Zhu, Xiao-Qing, et al. "Hydride, Hydrogen Atom, Proton, and Electron Transfer Driving Forces of Various Five-Membered Heterocyclic Organic Hydrides and Their Reaction Intermediates in Acetonitrile," J. Am. Chem. Soc., vol. 130, 2501-2516, 2008.
Sun, Qi, et al. "Synthesis and Biological Evaluation of Analogues of AKT (Protein Kinase B) Inhibitor-IV," J Med. Chem., vol. 54, 1126-1139, 2011.
Xing, B., et al., "Hydrogen/Oxygen Polymer Electrolyte Membrane Fuel Cells (PEMFCs) Based on Alkaline-Doped Polybenzimidazole (PBI)," Electrochem. Comm., 2(10), 697-702, 2000.

(Continued)

*Primary Examiner* — Timothy R Rozof
(74) *Attorney, Agent, or Firm* — Christensen O'Connor Johnson Kindness PLLC

(57) ABSTRACT

Provided herein are imidazolium polymers having steric hindrance at the 4-position of the imidazole moieties in the polymeric chain. The sterically-protected, N-methylated imidazolium polymers exhibit hydroxide stability in concentrated caustic solutions at elevated temperatures, such as at 100° C. and higher.

20 Claims, 15 Drawing Sheets

(56) References Cited

OTHER PUBLICATIONS

Hou, H., et al., "Alkali Doped Poly benzimidazole Membrane for Alkaline Direct Methanol Fuel Cell," In. J. Hydrogen Energy, 33(23), 7172-7176, 2008.
Novitski, D., et al., "Electrochemical Reduction of Dissolved Oxygen in Alkaline, Solid Polymer Electrolyte Films," J. Am. Chem. Soc., 138, 15465-15472, Nov. 2, 2016.
Weissbach, T., et al., "Simultaneous, Synergistic Control of Ion Exchange Capacity and Cross-Linking of Sterically-Protected Poly(benzimidazolium)s," Chem. Mater., 28(21), 8060-8070, Oct. 19, 2016.
Wright, A. G., et al., "Poly(phenylene) and m-Terphenyl as Powerful Protecting Groups for the Preparation of Stable Organic Hydroxides," Angew. Chem. Int. Ed., 55(15), 4818-4821, 2016.
Thomas, O. D., et al., "A Stable Hydroxide-Conducting Polymer," J. Am. Chem. Soc., 134 (26), 10753-10756, 2012.
Thomas, O. D., et al., "Anion Conducting Poly(Dialkyl Benzimidazolium) Salts," Poly. Chem., 2, 1641-1643, 2011.
Henkensmeier, D., et al., "Polybenzimidazolium-Based Solid Electrolytes," Macromolecular Materials and Engineering, vol. 296, 899-908, Jul. 22, 2011.
International Search Report and Written Opinion dated Jun. 13, 2018, issued in corresponding International Application No. PCT/CA2018/050436, filed Apr. 10, 2018, 10 pages.
Skalski, J., et al., Structurally-Defined, Sulfo-Phenylated, Oligophenylenes and Polyphenylenes, J. Am. Chem. Soc., 137, 12223-12226, 2015.
Adamski, M., et al., "Highly Stable, Low Gas Crossover, Proton-Conducting Phenylated Polyphenylenes," Angew. Chem. Int. Ed., 56, 9058-9061, 2017.
Lim, Y., et al., "Synthesis and Properties of Sulfonated Poly(Phyenylene Sulfone)s Without Ether Linkage by Diels-Alder Reaction for PEMFC Application," Electrochimica Acta 119, 16-23, 2014.
International Search Report and Written Opinion dated Dec. 21, 2017, issued in corresponding International Application No. PCT/US2017/44772, filed Aug. 1, 2017, 12 pages.
Partial International Search Report dated Feb. 26, 2020, issued in corresponding European Application No. 17837493.0, filed Aug. 1, 2017, 14 pages.
Valtcheva, I.B., et al., "Crosslinked Polybenzimidazole Membranes for Organic Solvent NanoFiltration (OSN) Analysis of Crosslinking Reaction Mechanism and Effects of Reaction Parameters," Journal of Membrane Science 493, Mar. 2015, 568-579.
Fan, J., et al., "Cationic Polyelectrolytes, Stable in 10 M KOHaq at 100° C.," Macro Letters 6(10):11089-1093, Sep. 2017.
International Search Report and Written Opinion dated Oct. 18, 2017, issued in corresponding International Application No. PCT/US2017/44554, filed Jul. 29, 2017, 7 pages.
Long, H., and B. Pivovar, "Hydroxide Degradation Pathways for Imidazolium Cations: A DFT Study," Journal of Physical Chemistry 118(19)19880-9888, Apr. 2014.
Wright, A.G., et al., "Hexamethyl-p-terphenyl poly(benzimidazolium): A Universal Hydroxide-Conducting Polymer for Energy Conversion Devices," Energy & Environmental Science 9(6):2130-2142, May 2016.
International Search Report, dated Mar. 8, 2017 in related International Application No. PCT/CA2017/050013, filed Jan. 6, 2017, 5 pages.
Extended European Search Report dated Sep. 6, 2017, issued in European Application No. 15780051.7, filed Apr. 15, 2015, 5 pages.
International Search Report dated Jul. 8, 2015, issued in corresponding International Application No. PCT/CA2015/000248, filed Apr. 15, 2015, 8 pages.
Extended European Search Report dated Sep. 4, 2019, issued in corresponding European Application No. EP 17735788.6, filed Jan. 6, 2017, 6 pages.
Richter, D., et al., "Kinetics of Hydride Abstractions from 2-Arylbenzimidazolines," Chemistry—An Asian Journal vol. 4: 1824-1829, 2009.
Written Opinion dated Mar. 8, 2017, issued in corresponding International Application No. PCT/CA2017/050013, filed Jan. 6, 2017, 6 pages.
European Search Report dated Oct. 31, 2 019, issued in corresponding European Application No. 17792325.7, filed May 1, 2017, 10 pages.

* cited by examiner

BTMA = benzyltrimethyl ammonium
CTAB = cetyltrimethyl ammonium
TMA = tetramethyl ammonium HB ($R^1=R^2=H$)
MeB ($R^1=R^2=Me$)
PhB ($R^1=Ph, R^2=H$)

HIm ($R^1=R^2=H$)
MeIm ($R^1=R^2=Me$)
PhIm ($R^1=Ph, R^2=H$)

STABLE POLY(IMIDAZOLIUM) HYDROXIDES

CROSS-REFERENCE(S) TO RELATED APPLICATION(S)

This application is a National Stage of PCT/US2017/044554, filed on Jul. 29, 2017, which claims the benefit of U.S. Provisional Application No. 62/368,667, filed Jul. 29, 2016, the disclosure of each of which is incorporated herein by reference in its entirety.

BACKGROUND

The fabrication of highly-stable cationic membranes and ionomers for energy conversion devices, such as alkaline hydrogen fuel cells, alkaline water electrolyzers, and redox-flow batteries, is crucial for their long-term function. While a number of materials have been developed for testing in such devices, no cationic membrane has been demonstrated to have good degradation resistance when subjected to extended exposure to alkaline solutions.

Cationic polyelectrolytes possess cationic groups either as a pendent functionality or integral to the main chain. Electroneutrality can be achieved by the presence of an anion, which is usually mobile when solvated. In recent years, the study of cationic polymers possessing hydroxide counter ions has gained prominence. However, organic-based polymer cations are prone to nucleophilic attack by hydroxide ions, which can destroy the anion-exchange capacity and hydroxide ion conductivity. Numerous cationic head groups have been explored with a view to increasing the stability of cationic polymers in highly basic media. For example, cobaltocenium-bearing polymers have been described in Gu, S. et al., *Sci. Rep.* 2015, 5, 11668 (incorporated herein by reference in its entirety) and exhibit exceptional stability. The stability of organic ammonium cations have been described by Marino, M. G.; Kreuer, K. D. *ChemSusChem* 2015, 8, 513 (incorporated herein by reference in its entirety), where aliphatic ammoniums were generally more stable than aromatic ammonium cations. A N-spirocyclic quaternary ammonium ionene that is stable in 1 M KOD/D$_2$O at 80° C. for 1800 h was described in Pham, T. H. et al., *J. Am. Chem. Soc.* 2017, 139, 2888, herein incorporated by reference in its entirety. A phosphonium cation, tetrakis(dialkylamino)phosphonium, which is stable in 1 M KOH at 80° C. up to 22 days, was described in Noonan, K. J. T. et al., *J. Am. Chem. Soc.* 2012, 134, 18161, incorporated herein by reference in its entirety. Metal-cation based anion exchange polymer membrane that showed good alkaline stability and tolerance to methanol was described in Zha, Y. et al., *J. Am. Chem. Soc.* 2012, 134, 4493. However, despite these advancements, cationic polymers stable in highly caustic solutions at elevated temperature (e.g., 10 M KOH, 100° C.) have proven elusive.

The stability of benzimidazolium and imidazolium small molecule model compounds has been shown to be correlated with the extent of steric hindrance proximal to the cationic moiety. For example, if mesitylene is substituted at the 2-position of 1,3-dimethylbenzimidazolium (MeB, Scheme 1), the small molecule possesses a half-life of 436 h in 3 M hydroxide at 80° C., as opposed to 1,3-dimethyl-2-phenyl-benzimidazolium (HB, Scheme 1), which has a half-life of <10 min in the same solution.

Scheme 1. Chemical structures of HB and MeB, where X$^-$ represents the counter anion.

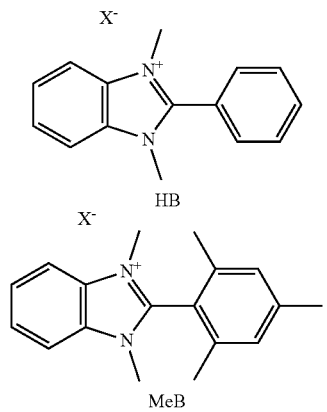

Dialkylated poly(benzimidazolium)s, which possess steric hindrance around the C2-position of the benzimidazolium ring, have been shown to exhibit much improved stability over their more "sterically-open" analogs. See, e.g., Thomas, O. D. et al., *J. Am. Chem. Soc.* 2012, 134, 10753; Wang, J. et al., S. *ACS Macro Lett.* 2014, 3, 444; Wright, A. G et al., *Angew. Chem. Int. Ed.* 2016, 55, 4818; Wright, A. G. et al., S. *Energy Environ. Sci.* 2016, 9, 2130; Thomas, O. D. et al., S. *Polym. Chem.* 2011, 2, 1641; and Henkensmeier, D. et al., *Macromol. Mater. Eng.* 2011, 296, 899; each of which is incorporated herein by reference in its entirety. Wright, A. G. et al., *Energy Environ. Sci.* 2016, 9, 2130, herein incorporated by reference in its entirety, described that benzimidazolium-based polymers protected by bulky mesityl groups are stable for extended periods in 1 M hydroxide solution at 80° C. but degrade much more rapidly in highly caustic, hot conditions; for example, 60% degradation was observed after 1 week immersion in 5 M NaOH at 80° C.

Cationic membranes having good hydroxide degradation resistance are therefore needed. The present disclosure seeks to fulfill these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a polymer including a repeating unit

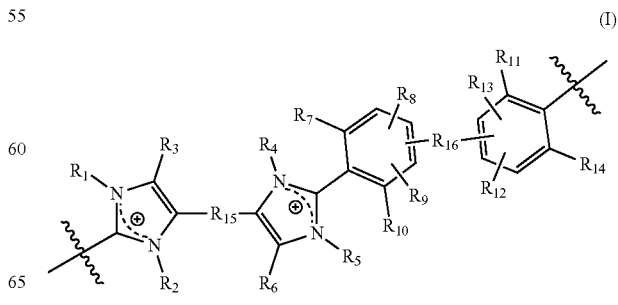

wherein:

$R_1$, $R_2$, $R_4$, and $R_5$ are each independently selected from absent, alkyl, perfluoroalkyl, heteroalkyl, aryl, and aralkyl; provided that
- at least one of $R_1$ and $R_2$ is selected from alkyl, perfluoroalkyl, heteroalkyl, aryl, and aralkyl,
- when one of $R_1$ and $R_2$ is absent, the imidazolyl group to which the absent $R_1$ or $R_2$ is connected is neutral; and
- at least one of $R_4$ and $R_5$ is selected from alkyl, perfluoroalkyl, heteroalkyl, aryl, and aralkyl; and
- when one of $R_4$ and $R_5$ is absent, the imidazolyl group to which the absent $R_4$ or $R_5$ is connected is neutral;

$R_3$ and $R_6$ are each independently selected from alkyl, perfluoroalkyl, heteroalkyl, aryl, aralkyl, and heteroaryl;

$R_{15}$ is selected from alkylene, perfluoroalkylene, heteroalkylene, arylene, aralkylene, and heteroarylene, each optionally substituted with 1, 2, 3, or 4 substituents independently selected from alkyl, perfluoroalkyl, heteroalkyl, and halo;

$R_{16}$ is selected from a bond, arylene, and heteroarylene, wherein said arylene and heteroarylene is each optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen, alkyl, perfluoroalkyl, and heteroalkyl.

In another aspect, the present disclosure features a polymer including a repeating unit of Formula (II):

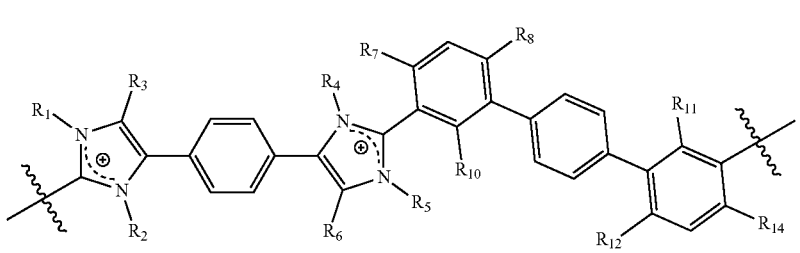

(II)

wherein:

$R_1$, $R_2$, $R_4$, and $R_5$ are each independently selected from absent, alkyl, perfluoroalkyl, heteroalkyl, aryl, and aralkyl; provided that
- at least one of $R_1$ and $R_2$ is selected from alkyl, perfluoroalkyl, heteroalkyl, aryl, and aralkyl,
- when one of $R_1$ and $R_2$ is absent, the imidazolyl group to which the absent $R_1$ or $R_2$ is connected is neutral; and
- at least one of $R_4$ and $R_5$ is selected from alkyl, perfluoroalkyl, heteroalkyl, aryl, and aralkyl; and
- when one of $R_4$ and $R_5$ is absent, the imidazolyl group to which the absent $R_4$ or $R_5$ is connected is neutral;

$R_3$ and $R_6$ are each independently selected from alkyl, perfluoroalkyl, heteroalkyl, aryl, aralkyl, and heteroaryl;

$R_7$, $R_{10}$, $R_{11}$, and $R_{14}$ are each independently selected from alkyl, perfluoroalkyl, and heteroalkyl; and $R_8$ and $R_{12}$ are each independently selected from hydrogen, alkyl, perfluoroalkyl, and heteroalkyl.

In yet another aspect, the present disclosure features a polymer including a repeating unit of Formula (III-A):

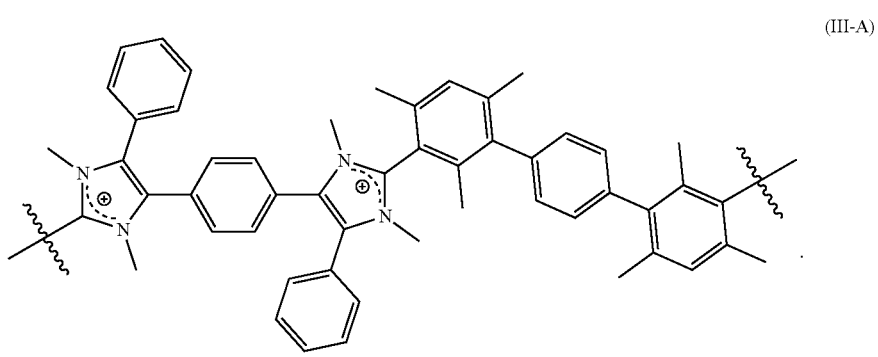

(III-A)

In some embodiments, the polymer including a repeating unit of Formula (III-A) further includes a repeating unit of Formula (III-B):

(III-B)

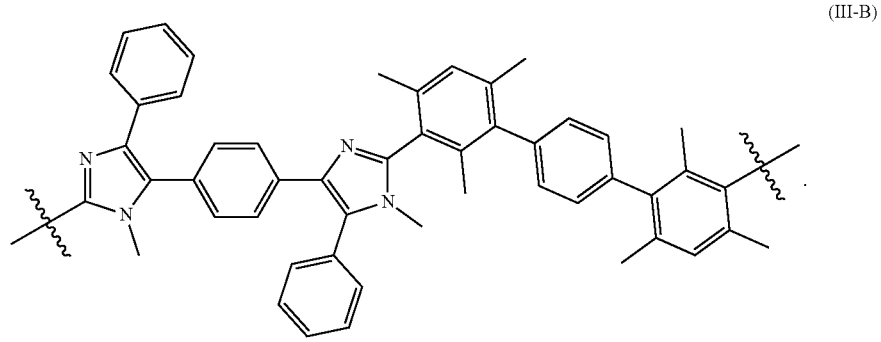 [SMILES: *c1c(C)cc(C)c(-c2ccc(-c3c(C)cc(C)c(-c4nc(-c5ccc(-c6c(-c7ccccc7)nc(*)n6C)cc5)c(-c5ccccc5)n4C)c3C)cc2)c1C]

In some embodiments, the polymer including a repeating unit of Formula (III-A) and/or (III-B) further includes a repeating unit of Formula (III-C):

(III-C)

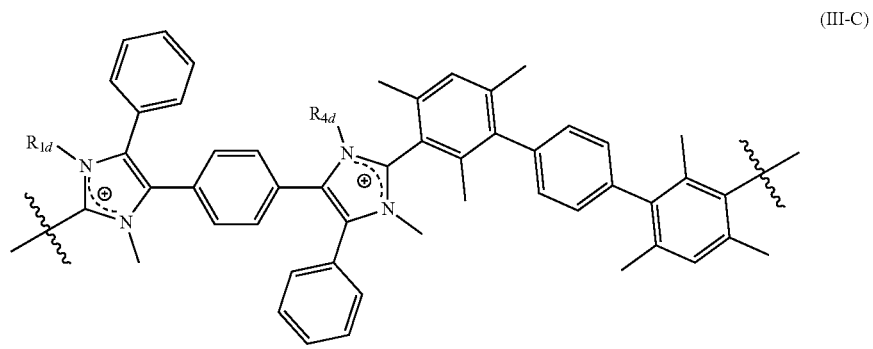

wherein one of $R_{1d}$ and $R_{4d}$ is absent, and the remaining $R_{1d}$ or $R_{4d}$ is methyl; and the imidazolyl group to which the absent $R_{1d}$ or $R_{4d}$ is connected is neutral.

In yet a further aspect, the present disclosure features a random polymer, including repeating units of Formula (IV-A), (IV-B), and (IV-C):

(IV-A)

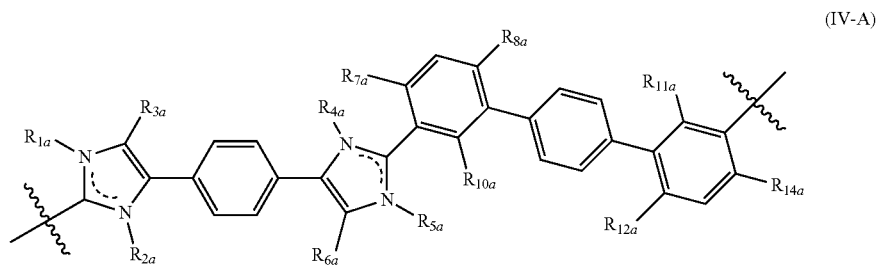

(IV-B)

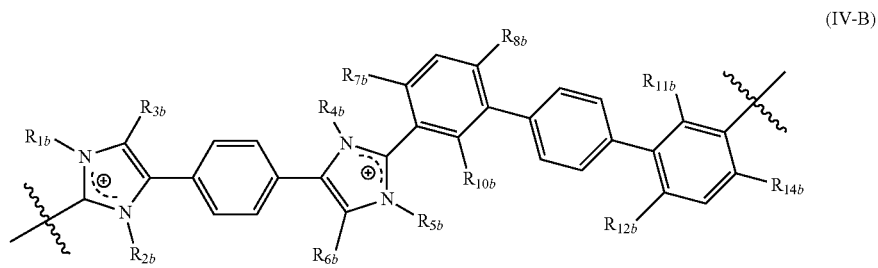

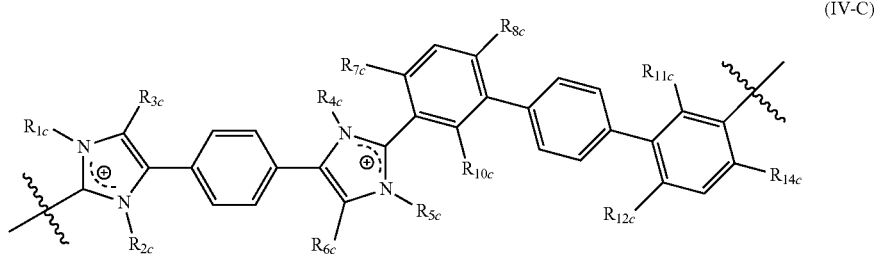

(IV-C)

wherein one of $R_{1a}$ and $R_{2a}$ is absent and the remaining $R_{1a}$ or $R_{2a}$ is selected from alkyl, perfluoroalkyl, heteroalkyl, aryl, and aralkyl;

one of $R_{4a}$ and $R_{5a}$ is absent and the remaining $R_{4a}$ or $R_{5a}$ is selected from alkyl, perfluoroalkyl, heteroalkyl, aryl, and aralkyl;

one of $R_{1b}$, $R_{2b}$, $R_{4b}$, and $R_{5b}$ is absent and the imidazolyl group to which the absent $R_{1b}$, $R_{2b}$, $R_{4b}$, or $R_{5b}$ is connected is neutral, and the remaining three of $R_{1b}$, $R_{2b}$, $R_{4b}$, and $R_{5b}$ are each independently selected from alkyl, perfluoroalkyl, heteroalkyl, aryl, and aralkyl;

$R_{1c}$, $R_{2c}$, $R_{4c}$, and $R_{5c}$ are each independently selected from alkyl, perfluoroalkyl, heteroalkyl, aryl, and aralkyl;

$R_{3a}$, $R_{6a}$, $R_{3b}$, $R_{6b}$, $R_{3c}$, and $R_{6c}$ are each independently selected from alkyl, perfluoroalkyl, heteroalkyl, aryl, aralkyl, and heteroaryl;

$R_{7a}$, $R_{10a}$, $R_{11a}$, $R_{14a}$, $R_{7b}$, $R_{10b}$, $R_{11b}$, $R_{14b}$, $R_{7c}$, $R_{10c}$, $R_{11c}$, and $R_{14c}$ are each independently selected from alkyl, perfluoroalkyl, and heteroalkyl; and $R_{8a}$, $R_{12a}$, $R_{8b}$, $R_{12b}$, $R_{8c}$, and $R_{12c}$ are each independently selected from hydrogen, alkyl, perfluoroalkyl, and heteroalkyl;

wherein the polymer includes m mole percentage repeating units of Formula (IV-A), n mole percentage repeating units of Formula (IV-B), and p mole percentage repeating units of Formula (IV-C), and m is from 0 mole percent to 60 mole percent, n+p is 40 mole percent to 100 mole percent, and $$m+n+p=100\%.$$

In a further aspect, the present disclosure features an ionic membrane including any of the above-described polymers. The present disclosure also features an ionomer including any of the above-described polymers. The ionomer can be incorporated into a catalyst layer of a fuel cell, of an electrolyzer, or of other electrochemical devices.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1A:
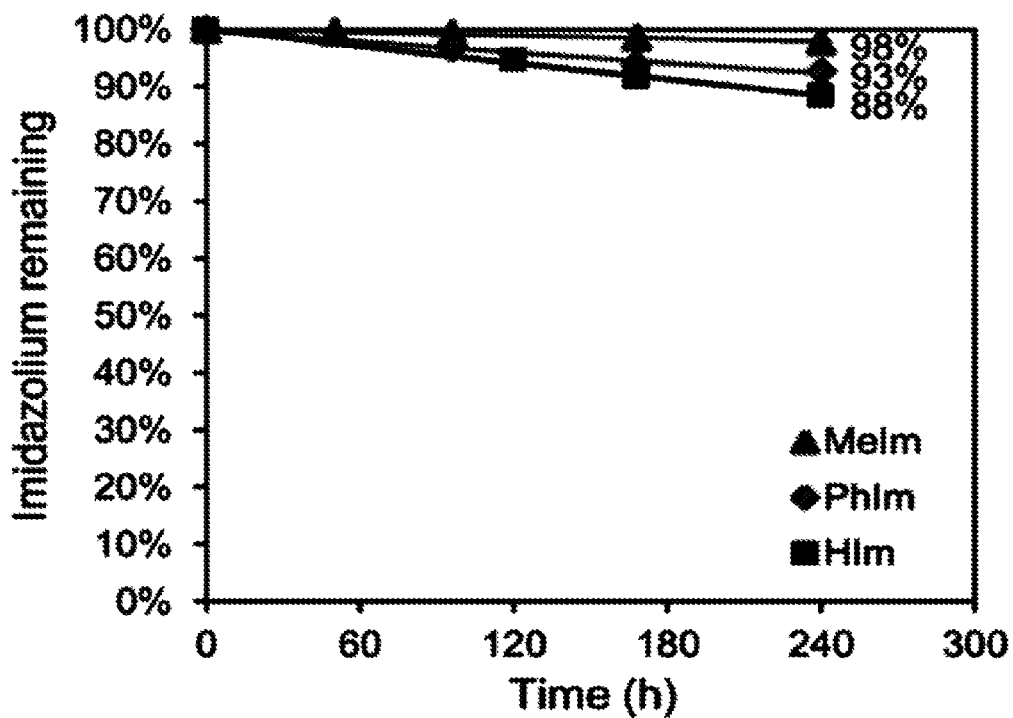
FIG. 1A is a graph showing percent imidazolium remaining for embodiments of imidazolium small molecules (e.g., HIm, MeIm, and PhIm) at a concentration of 0.02 M exposed to a 3 M NaOD solution containing 70 wt % $CD_3OD$ in $D_2O$ at 80° C. over time, as determined by $^1H$ NMR spectroscopy.

Provided herein are imidazolium polymers having steric hindrance at the 4-position of the imidazole moieties in the polymeric chain. The sterically-protected, N-methylated imidazolium polymers exhibit hydroxide stability in concentrated caustic solutions at elevated temperatures, such as at 100° C. and higher.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a straight or branched hydrocarbon groups. In some embodiments, alkyl has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkyl groups include methyl, ethyl, propyl (e.g., n-propyl, isopropyl), butyl (e.g., n-butyl, sec-butyl, and tert-butyl), pentyl (e.g., n-pentyl, tert-pentyl, neopentyl, isopentyl, pentan-2-yl, pentan-3-yl), and hexyl (e.g., n-hexyl and isomers) groups.

As used herein, the term "alkylene" refers to a linking alkyl group.

As used herein, the term "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, the term "cycloalkylene" refers to a linking cycloalkyl group.

As used herein, the term "perfluoroalkyl" refers to straight or branched fluorocarbon chains. In some embodiments, perfluoroalkyl has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkyl groups include trifluoromethyl, pentafluoroethyl, etc.

As used herein, the term "perfluoroalkylene" refers to a linking perfluoroalkyl group.

As used herein, the term "heteroalkyl" refers to a straight or branched chain alkyl groups and where one or more of the carbon atoms is replaced with a heteroatom selected from O, N, or S. In some embodiments, heteroalkyl alkyl has 1 to 10 carbon atoms (e.g., 1 to 8 carbon atoms, 1 to 6 carbon atoms, 1 to 3 carbon atoms, 1 or 2 carbon atoms, or 1 carbon atom).

As used herein, the term "heteroalkylene" refers to a linking heteroalkyl group.

As used herein, the term "alkoxy" refers to an alkyl or cycloalkyl group as described herein bonded to an oxygen atom. In some embodiments, alkoxy has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkoxy groups include methoxy, ethoxy, propoxy, and isopropoxy groups.

As used herein, the term "perfluoroalkoxy" refers to a perfluoroalkyl or cyclic perfluoroalkyl group as described herein bonded to an oxygen atom. In some embodiments, perfluoroalkoxy has 1 to 10 carbon atoms (e.g., 1 to 8 carbon atoms, 1 to 6 carbon atoms, 1 to 3 carbon atoms, 1 or 2 carbon atoms, or 1 carbon atom). Representative perfluoroalkoxy groups include trifluoromethoxy, pentafluoroethoxy, etc.

As used herein, the term "aryl" refers to an aromatic hydrocarbon group having 6 to 10 carbon atoms. Representative aryl groups include phenyl groups. In some embodiments, the term "aryl" includes monocyclic or polycyclic (e.g., having 2, 3, or 4 fused rings) aromatic hydrocarbons such as, for example, phenyl, naphthyl, anthracenyl, phenanthrenyl, indanyl, and indenyl.

As used herein, the term "arylene" refers to a linking aryl group.

As used herein, the term "aralkyl" refers to an alkyl or cycloalkyl group as defined herein with an aryl group as defined herein substituted for one of the alkyl hydrogen atoms. A representative aralkyl group is a benzyl group.

As used herein, the term "aralkylene" refers to a linking aralkyl group.

As used herein, the term "heteroaryl" refers to a 5- to 10-membered aromatic monocyclic or bicyclic ring containing 1-4 heteroatoms selected from O, S, and N. Representative 5- or 6-membered aromatic monocyclic ring groups include pyridine, pyrimidine, pyridazine, furan, thiophene, thiazole, oxazole, and isooxazole. Representative 9- or 10-membered aromatic bicyclic ring groups include benzofuran, benzothiophene, indole, pyranopyrrole, benzopyran, quionoline, benzocyclohexyl, and naphthyridine.

As used herein, the term "heteroarylene" refers to a linking heteroaryl group.

As used herein, the term "halogen" or "halo" refers to fluoro, chloro, bromo, and iodo groups.

As used herein, when an imidazolium is positively charged, for example, as illustrated below,

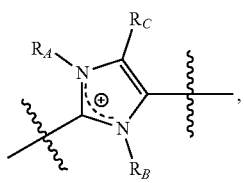

it is understood that the illustrated structure encompasses a double bond that may be located in one of two positions and the positive charge is consequently localized on one of the two imidazolium nitrogen atoms:

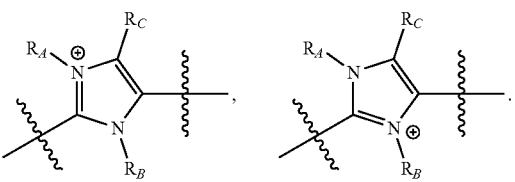

As used herein, the term "bulky group" refers to a group providing steric bulk by having a size at least as large as a methyl group.

As used herein, the term "copolymer" refers to a polymer that is the result of polymerization of two or more different monomers. The number and the nature of each constitutional unit can be separately controlled in a copolymer. The constitutional units can be disposed in a purely random, an alternating random, a regular alternating, a regular block, or a random block configuration unless expressly stated to be otherwise. A purely random configuration can, for example, be: x-x-y-z-x-y-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . . A regular block configuration (i.e., a block copolymer) has the following general configuration: . . . x-x-x-y-y-y-z-z-z-x-x-x . . . , while a random block configuration has the general configuration: . . . x-x-x-z-z-x-x-y-y-y-z-z-z-x-x-z-z-z- . . . .

As used herein, the term "random copolymer" is a copolymer having an uncontrolled mixture of two or more constitutional units. The distribution of the constitutional units throughout a polymer backbone (or main chain) can be a statistical distribution, or approach a statistical distribution, of the constitutional units. In some embodiments, the distribution of one or more of the constitutional units is favored.

As used herein, the term "constitutional unit" of a polymer refers to an atom or group of atoms in a polymer, comprising a part of the chain together with its pendant atoms or groups of atoms, if any. The constitutional unit can refer to a repeating unit. The constitutional unit can also refer to an end group on a polymer chain. For example, the constitutional unit of polyethylene glycol can be —$CH_2CH_2O$— corresponding to a repeating unit, or —$CH_2CH_2OH$ corresponding to an end group.

As used herein, the term "repeating unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, the term "anionic" refers to a functional group that is negatively charged, or ionizable to a negatively charged moiety under physiological conditions. Examples of anionic groups include carboxylate, sulfate, sulfonate, phosphate, etc.

As used herein, "degree of methylation" (dm) refers to the percentage of N-methylation of, for example, an embodiment of a polymer of the present disclosure. Thus, if all the ring-forming nitrogen atoms in the imidazole moieties of a polymer are methylated, then the degree of methylation is 100%. If half of the ring-forming nitrogen atoms in the imidazole moieties of a polymer are methylated, then the degree of methylation is 50%.

As used herein, the term "consisting essentially of" or "consists essentially of" refers to a composition including the components of which it consists essentially as well as other components, provided that the other components do not materially affect the essential characteristics of the composition. Typically, a composition consisting essentially of certain components will comprise greater than or equal to 95 wt % of those components or greater than or equal to 99 wt % of those components.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Polymers

The present disclosure features a polymer including (or consisting essentially of, or consisting of) a repeating unit of Formula (I):

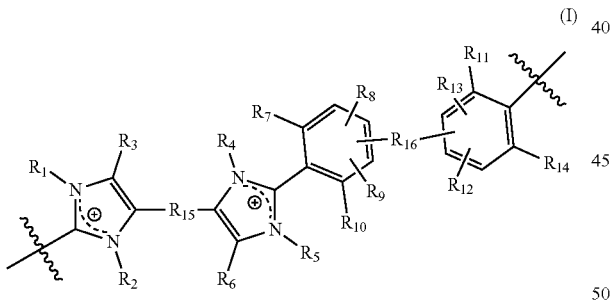

(I)

wherein:

$R_1$, $R_2$, $R_4$, and $R_5$ are each independently selected from absent, alkyl, perfluoroalkyl, heteroalkyl, aryl, and aralkyl; provided that
  at least one of $R_1$ and $R_2$ is selected from alkyl, perfluoroalkyl, heteroalkyl, aryl, and aralkyl,
  when one of $R_1$ and $R_2$ is absent, the imidazolyl group to which the absent $R_1$ or $R_2$ is connected (i.e., the imidazolyl group having one of $R_1$ or $R_2$, but not the other) is neutral; and
  at least one of $R_4$ and $R_5$ is selected from alkyl, perfluoroalkyl, heteroalkyl, aryl, and aralkyl; and
  when one of $R_4$ and $R_5$ is absent, the imidazolyl group to which the absent $R_4$ or $R_5$ is connected (i.e., the imidazolyl group having one of $R_4$ or $R_5$, but not the other) is neutral;

$R_3$ and $R_6$ are each independently selected from alkyl, perfluoroalkyl, heteroalkyl, aryl, aralkyl, and heteroaryl;

$R_{15}$ is selected from alkylene, perfluoroalkylene, heteroalkylene, arylene, aralkylene, and heteroarylene, each optionally substituted with 1, 2, 3, or 4 substituents independently selected from alkyl, perfluoroalkyl, heteroalkyl, and halo;

$R_{16}$ is selected from a bond, arylene, and heteroarylene, wherein said arylene and heteroarylene is each optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen (H), alkyl, perfluoroalkyl, and heteroalkyl.

In some embodiments, the polymer including (or consisting essentially of, or consisting of) a repeating unit of Formula (I) includes a repeating unit of Formula (I-A):

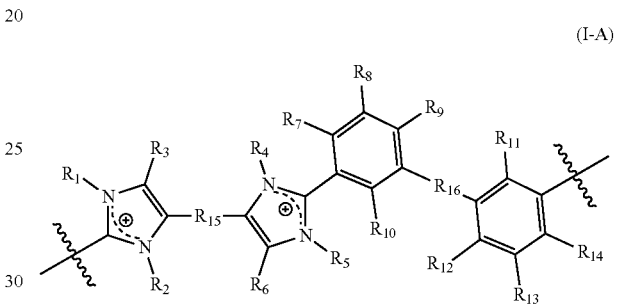

(I-A)

wherein:

$R_1$, $R_2$, $R_4$, and $R_5$ are each independently selected from absent, alkyl, perfluoroalkyl, heteroalkyl, aryl, and aralkyl; provided that
  at least one of $R_1$ and $R_2$ is selected from alkyl, perfluoroalkyl, heteroalkyl, aryl, and aralkyl,
  when one of $R_1$ and $R_2$ is absent, the imidazolyl group to which the absent $R_1$ or $R_2$ is connected (i.e., the imidazolyl group having one of $R_1$ or $R_2$, but not the other) is neutral;
  at least one of $R_4$ and $R_5$ is selected from alkyl, perfluoroalkyl, heteroalkyl, aryl, and aralkyl; and
  when one of $R_4$ and $R_5$ is absent, the imidazolyl group to which the absent $R_4$ or $R_5$ is connected (i.e., the imidazolyl group having one of $R_4$ or $R_5$, but not the other) is neutral;

$R_3$ and $R_6$ are each independently selected from alkyl, perfluoroalkyl, heteroalkyl, aryl, aralkyl, and heteroaryl;

$R_{15}$ is selected from alkylene, perfluoroalkylene, heteroalkylene, arylene, aralkylene, and heteroarylene, each optionally substituted with 1, 2, 3, or 4 substituents independently selected from alkyl, perfluoroalkyl, heteroalkyl, and halo;

$R_{16}$ is selected from a bond, arylene, and heteroarylene, wherein said arylene and heteroarylene is each optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen (H), alkyl, perfluoroalkyl, and heteroalkyl.

In some embodiments, the polymer including (or consisting essentially of, or consisting of) a repeating unit of Formula (I) includes, or the polymer including repeating unit(s) of Formula (I-A) further includes, a repeating unit of Formula (I-B):

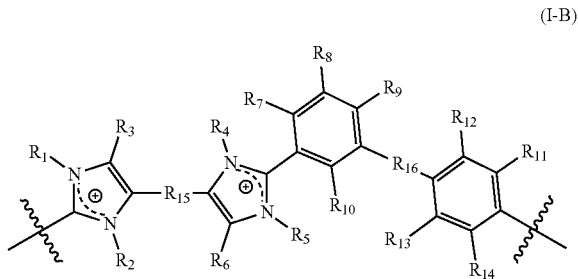

(I-B)

wherein:

R₁, R₂, R₄, and R₅ are each independently selected from absent, alkyl, perfluoroalkyl, heteroalkyl, aryl, and aralkyl;
provided that
at least one of R₁ and R₂ is selected from alkyl, perfluoroalkyl, heteroalkyl, aryl, and aralkyl,
when one of R₁ and R₂ is absent, the imidazolyl group to which the absent R₁ or R₂ is connected (i.e., the imidazolyl group having one of R₁ or R₂, but not the other) is neutral; and
at least one of R₄ and R₅ is selected from alkyl, perfluoroalkyl, heteroalkyl, aryl, and aralkyl; and
when one of R₄ and R₅ is absent, the imidazolyl group to which the absent R₄ or R₅ is connected (i.e., the imidazolyl group having one of R₄ or R₅, but not the other) is neutral;

R₃ and R₆ are each independently selected from alkyl, perfluoroalkyl, heteroalkyl, aryl, aralkyl, and heteroaryl;

R₁₅ is selected from alkylene, perfluoroalkylene, heteroalkylene, arylene, aralkylene, and heteroarylene, each optionally substituted with 1, 2, 3, or 4 substituents independently selected from alkyl, perfluoroalkyl, heteroalkyl, and halo;

R₁₆ is selected from a bond, arylene, and heteroarylene, wherein said arylene and heteroarylene is each optionally substituted with 1, 2, 3, or 4 substituents independently selected from alkyl, perfluoroalkyl, heteroalkyl, and halo;

R₇, R₁₀, R₁₁, and R₁₄ are each independently selected from alkyl, perfluoroalkyl, and heteroalkyl; and R₈, R₉, R₁₂, and R₁₃ are each independently selected from hydrogen (H), alkyl, perfluoroalkyl, and heteroalkyl.

In some embodiments, the polymer including (or consisting essentially of, or consisting of) a repeating unit of Formula (I) includes, or the polymer including repeating unit(s) of Formula (I-A) and/or Formula (I-B) further includes a repeating unit of Formula (I-C):

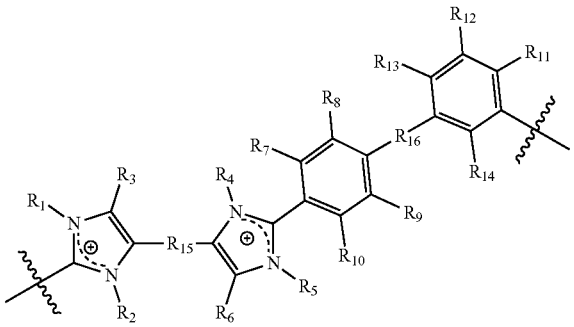

(I-C)

wherein:

R₁, R₂, R₄, and R₅ are each independently selected from absent, alkyl, perfluoroalkyl, heteroalkyl, aryl, and aralkyl;
provided that
at least one of R₁ and R₂ is selected from alkyl, perfluoroalkyl, heteroalkyl, aryl, and aralkyl,
when one of R₁ and R₂ is absent, the imidazolyl group to which the absent R₁ and R₂ is connected (i.e., the imidazolyl group having one of R₁ or R₂, but not the other) is neutral; and
at least one of R₄ and R₅ is selected from alkyl, perfluoroalkyl, heteroalkyl, aryl, and aralkyl; and
when one of R₄ and R₅ is absent, the imidazolyl group to which the absent R₄ or R₅ is connected (i.e., the imidazolyl group having one of R₄ or R₅, but not the other) is neutral;

R₃ and R₆ are each independently selected from alkyl, perfluoroalkyl, heteroalkyl, aryl, aralkyl, and heteroaryl;

R₁₅ is selected from alkylene, perfluoroalkylene, heteroalkylene, arylene, aralkylene, and heteroarylene, each optionally substituted with 1, 2, 3, or 4 substituents independently selected from alkyl, perfluoroalkyl, heteroalkyl, and halo;

R₁₆ is selected from a bond, arylene, and heteroarylene, wherein said arylene and heteroarylene is each optionally substituted with 1, 2, 3, or 4 substituents independently selected from alkyl, perfluoroalkyl, heteroalkyl, and halo;

R₇, R₁₀, R₁₁, and R₁₄ are each independently selected from alkyl, perfluoroalkyl, and heteroalkyl; and R₈, R₉, R₁₂, and R₁₃ are each independently selected from hydrogen (H), alkyl, perfluoroalkyl, and heteroalkyl.

In some embodiments, the polymer including (or consisting essentially of, or consisting of) a repeating unit of Formula (I) includes, or the polymer including repeating unit(s) of Formula Formula (I-A), Formula (I-B), and/or Formula (I-C) further includes a repeating unit of Formula (I-D):

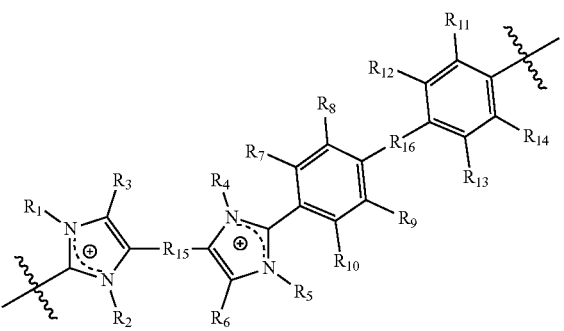

(I-D)

wherein:

R₁, R₂, R₄, and R₅ are each independently selected from absent, alkyl, perfluoroalkyl, heteroalkyl, aryl, and aralkyl;
provided that
at least one of R₁ and R₂ is selected from alkyl, perfluoroalkyl, heteroalkyl, aryl, and aralkyl,
when one of R₁ and R₂ is absent, the imidazolyl group to which the absent R₁ or R₂ is connected (i.e., the imidazolyl group having one of R₁ or R₂, but not the other) is neutral; and
at least one of R₄ and R₅ is selected from alkyl, perfluoroalkyl, heteroalkyl, aryl, and aralkyl; and
when one of R₄ and R₅ is absent, the imidazolyl group to which the absent R₄ or R₅ is connected (i.e., the imidazolyl group having one of R₄ or R₅, but not the other) is neutral;

$R_3$ and $R_6$ are each independently selected from alkyl, perfluoroalkyl, heteroalkyl, aryl, aralkyl, and heteroaryl;

$R_{15}$ is selected from alkylene, perfluoroalkylene, heteroalkylene, arylene, aralkylene, and heteroarylene, each optionally substituted with 1, 2, 3, or 4 substituents independently selected from alkyl, perfluoroalkyl, heteroalkyl, and halo;

$R_{16}$ is selected from a bond, arylene, and heteroarylene, wherein said arylene and heteroarylene is each optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen (H), alkyl, perfluoroalkyl, and heteroalkyl.

The polymer of Formula (I) can have a mixture of repeating units of Formulas (I-A), (I-B), (I-C), and/or (I-D). For example, the polymer can include repeating units of Formulas (I-A), (I-B), (I-C), and (I-D); Formulas (I-A), (I-B), and (I-C); Formulas (I-A), (I-B), and (I-D); Formulas (I-A), (I-C), and (I-D); Formulas (I-B), (I-C), (I-D); Formulas (I-A) and (I-B); Formulas (I-A) and (I-C); Formulas (I-A) and (I-D); Formulas (I-B) and (I-C); Formulas (I-B) and (I-D); Formulas (I-C) and (I-D); Formula (I-A); Formula (I-B); Formula (I-C); or Formula (I-D).

In any of the above-mentioned embodiments of polymers including (or consisting essentially of, or consisting of) a repeating unit of Formula (I); or including repeating unit(s) of Formula (I-A), (I-B), (I-C), and/or (I-D), $R_1$, $R_2$, $R_4$, and $R_5$ can each be independently selected from absent, alkyl, perfluoroalkyl, heteroalkyl, and aryl; provided that: at least one of $R_1$ and $R_2$ is selected from alkyl, perfluoroalkyl, heteroalkyl, and aryl; and at least one of $R_4$ and $R_5$ is selected from alkyl, perfluoroalkyl, heteroalkyl, and aryl. For example, $R_1$, $R_2$, $R_4$, and $R_5$ can each independently be selected from absent, alkyl, perfluoroalkyl, and heteroalkyl; provided that: at least one of $R_1$ and $R_2$ is selected from alkyl, perfluoroalkyl, and heteroalkyl; and at least one of $R_4$ and $R_5$ is selected from alkyl, perfluoroalkyl, and heteroalkyl. In some embodiments, $R_1$, $R_2$, $R_4$, and $R_5$ are each independently selected from absent, methyl, and trifluoromethyl; provided that: at least one of $R_1$ and $R_2$ is selected from methyl and trifluoromethyl; and at least one of $R_4$ and $R_5$ is selected from methyl and trifluoromethyl.

In any of the above-mentioned embodiments of polymers including (or consisting essentially of, or consisting of) a repeating unit of Formula (I); or including repeating unit(s) of Formula (I-A), (I-B), (I-C), and/or (I-D), $R_3$ and $R_6$ can each independently aryl. For example, $R_3$ and $R_6$ can each independently phenyl. In some embodiments, $R_3$ and $R_6$ are each independently ethyl or methyl. In some embodiments, $R_3$ and $R_6$ are each independently methyl.

In any of the above-mentioned embodiments of polymers including (or consisting essentially of, or consisting of) a repeating unit of Formula (I); or including repeating unit(s) of Formula (I-A), (I-B), (I-C), and/or (I-D), $R_{15}$ and $R_{16}$ can each independently be selected from arylene and heteroarylene, each optionally substituted with 1, 2, 3, or 4 substituents independently selected from alkyl and halo. For example, $R_{15}$ and $R_{16}$ can each independently be arylene, optionally substituted with 1, 2, 3, or 4 substituents independently selected from alkyl and halo. For example, $R_{15}$ and $R_{16}$ can each be phenylene, optionally substituted with 1, 2, 3, or 4 substituents independently selected from alkyl and halo. In some embodiments, $R_{15}$ and $R_{16}$ are each phenylene.

In any of the above-mentioned embodiments of polymers including (or consisting essentially of, or consisting of) a repeating unit of Formula (I); or including repeating unit(s) of Formula (I-A), (I-B), (I-C), and/or (I-D), $R_7$, $R_{10}$, $R_{11}$, and $R_{14}$ can each independently be alkyl. For example, $R_7$, $R_{10}$, $R_{11}$, and $R_{14}$ can each independently be methyl or ethyl. For example, $R_7$, $R_{10}$, $R_{11}$, and $R_{14}$ can each independently be methyl.

In any of the above-mentioned embodiments of polymers including (or consisting essentially of, or consisting of) a repeating unit of Formula (I); or including repeating unit(s) of Formula (I-A), (I-B), (I-C), and/or (I-D), the polymer can include one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof, the one or more anions $X^-$ counterbalance one or more positive charges in the polymer. In some embodiments, the polymer includes one or more anions $X^-$ selected from iodide, bromide, chloride, fluoride, triiodide, hydroxide, carbonate, bicarbonate, sulfate, phosphate, triflate, tosylate, tetrakis(3,5-bis(trifluoromethyl)phenyl)borate, bis(trifluoromethane)sulfonamide, and any combination thereof, where the one or more anions $X^-$ counterbalance one or more positive charges in the polymer. In some embodiments, the polymer includes one or more anions $X^-$ selected from iodide, bromide, chloride, fluoride, hydroxide, carbonate, bicarbonate, and any combination thereof, where the one or more anions X-counterbalance one or more positive charges in the polymer. In some embodiments, the polymer includes one or more anions $X^-$ selected from iodide, bromide, chloride, hydroxide, and any combination thereof, where the one or more anions $X^-$ counterbalance one or more positive charges in the polymer. In some embodiments, the polymer includes one or more anions $X^-$ selected from iodide, hydroxide, and any combination thereof, where the one or more anions $X^-$ counterbalance one or more positive charges in the polymer. In some embodiments, the polymer includes one or more hydroxide, where the one or more hydroxide counterbalance one or more positive charges in the polymer.

The present disclosure also provides a polymer including (or consisting essentially of, or consisting of) a repeating unit of Formula (II):

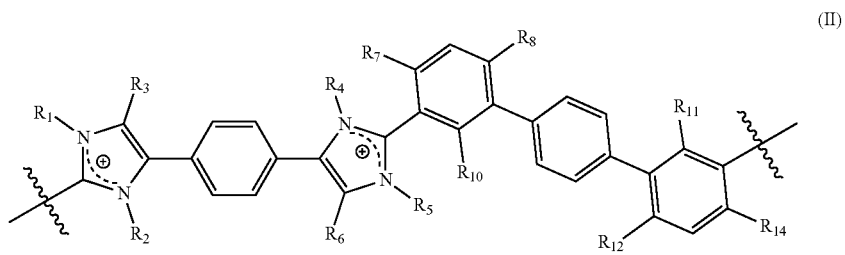

wherein:

$R_1$, $R_2$, $R_4$, and $R_5$ are each independently selected from absent, alkyl, perfluoroalkyl, heteroalkyl, aryl, and aralkyl; provided that at least one of $R_1$ and $R_2$ is selected from alkyl, perfluoroalkyl, heteroalkyl, aryl, and aralkyl, when one of $R_1$ and $R_2$ is absent, the imidazolyl group to which the absent $R_1$ or $R_2$ is connected (i.e., the imidazolyl group having one of $R_1$ or $R_2$, but not the other) is neutral; and at least one of $R_4$ and $R_5$ is selected from alkyl, perfluoroalkyl, heteroalkyl, aryl, and aralkyl; and when one of $R_4$ and $R_5$ is absent, the imidazolyl group to which the absent $R_4$ or $R_5$ is connected (i.e., the imidazolyl group having one of $R_4$ or $R_5$, but not the other) is neutral;

$R_3$ and $R_6$ are each independently selected from alkyl, perfluoroalkyl, heteroalkyl, aryl, aralkyl, and heteroaryl;

$R_7$, $R_{10}$, $R_{11}$, and $R_{14}$ are each independently selected from alkyl, perfluoroalkyl, and heteroalkyl; and $R_8$ and $R_{12}$ are each independently selected from hydrogen (H), alkyl, perfluoroalkyl, and heteroalkyl.

In some embodiments, for the above-described polymer including (or consisting essentially of, or consisting of) a repeating unit of Formula (II), $R_1$, $R_2$, $R_4$, and $R_5$ are each independently selected from absent, alkyl, perfluoroalkyl, and heteroalkyl; provided that: at least one of $R_1$ and $R_2$ is selected from alkyl, perfluoroalkyl, and heteroalkyl, and at least one of $R_4$ and $R_5$ is selected from alkyl, perfluoroalkyl, and heteroalkyl. For example, $R_1$, $R_2$, $R_4$, and $R_5$ can each independently selected from absent, methyl, and trifluoromethyl; provided that: at least one of $R_1$ and $R_2$ is selected from methyl and trifluoromethyl, and at least one of $R_4$ and $R_5$ is selected from methyl and trifluoromethyl.

In some embodiments, for any of the above-mentioned embodiments of polymers including (or consisting essentially of, or consisting of) a repeating unit of Formula (II), $R_3$ and $R_6$ are each independently aryl. For example, $R_3$ and $R_6$ can each be independently phenyl. In some embodiments, $R_3$ and $R_6$ are each independently methyl or ethyl. In some embodiments, $R_3$ and $R_6$ are each independently methyl.

In some embodiments, for any of the above-mentioned embodiments of polymers including (or consisting essentially of, or consisting of) a repeating unit of Formula (II), $R_7$, $R_8$, $R_{10}$, $R_{11}$, $R_{12}$, and $R_{14}$ are each independently alkyl. For example, $R_7$, $R_8$, $R_{10}$, $R_{11}$, $R_{12}$, and $R_{14}$ are each independently methyl or ethyl. For example, $R_7$, $R_8$, $R_{10}$, $R_{11}$, $R_{12}$, and $R_{14}$ are each independently methyl.

In some embodiments, for any of the above-mentioned embodiments of polymers including (or consisting essentially of, or consisting of) a repeating unit of Formula (II), the polymer includes one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof, where the one or more anions $X^-$ counterbalance one or more positive charges in the polymer. For example, the one or more anions $X^-$ can be selected from iodide, bromide, chloride, fluoride, triiodide, hydroxide, carbonate, bicarbonate, sulfate, phosphate, triflate, tosylate, tetrakis(3,5-bis(trifluoromethyl)phenyl)borate, bis(trifluoromethane)sulfonamide, and any combination thereof, where the one or more anions $X^-$ counterbalance one or more positive charges in the polymer. In some embodiments, one or more anions $X^-$ are selected from iodide, bromide, chloride, fluoride, hydroxide, carbonate, bicarbonate, and any combination thereof, where the one or more anions $X^-$ counterbalance one or more positive charges in the polymer. In some embodiments, the polymer includes one or more anions $X^-$ selected from iodide, bromide, chloride, hydroxide, and any combination thereof, where the one or more anions $X^-$ counterbalance one or more positive charges in the polymer. In some embodiments, the polymer includes one or more anions $X^-$ selected from iodide, hydroxide, and any combination thereof, where the one or more anions $X$-counterbalance one or more positive charges in the polymer. In some embodiments, the polymer includes one or more hydroxide, where the one or more hydroxide counterbalance one or more positive charges in the polymer.

The present disclosure further provides a polymer including a repeating unit of Formula (III-A):

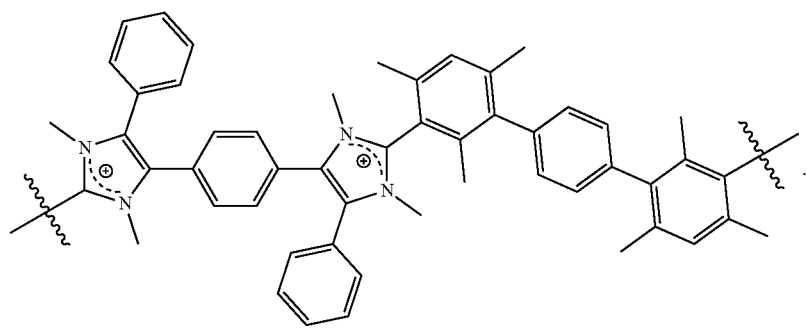

(III-A)

In some embodiments, the polymer including a repeating unit of Formula (III-A) further includes a repeating unit of Formula (III-B):

(IIIB)

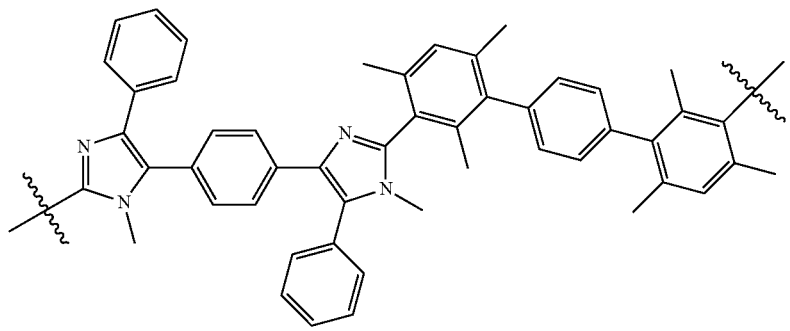

In some embodiments, the polymer including a repeating unit of Formula (III-A), or including repeating units of Formulas (III-A) and (III-B), further includes a repeating unit of Formula (III-C):

(III-C)

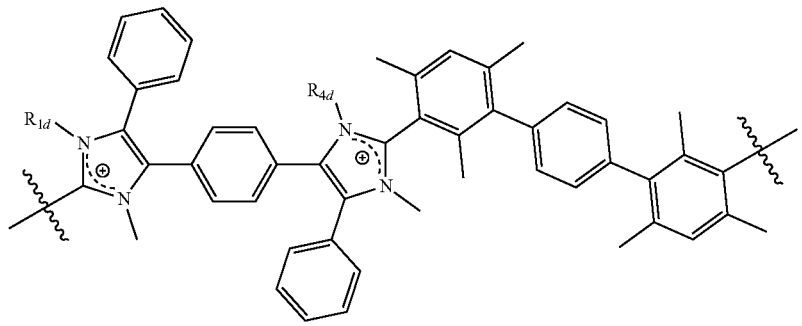

wherein one of $R_{1d}$ and $R_{4d}$ is absent, and the remaining $R_{1d}$ or $R_{4d}$ is methyl; and the imidazolyl group to which the absent $R_{1d}$ or $R_{4d}$ is connected (i.e., the imidazolyl group where one of its $R_{1d}$ or $R_{4d}$ is absent) is neutral.

In some embodiments, for any of the above-described polymers including (or consisting essentially of, or consisting of) a repeating unit of Formula (III-A), (III-B), and/or (III-C), the polymer includes one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof, where the one or more anions $X^-$ counterbalances one or more positive charges in the polymer. In some embodiments, one or more anions $X^-$ are selected from iodide, bromide, chloride, fluoride, triiodide, hydroxide, carbonate, bicarbonate, sulfate, phosphate, triflate, tosylate, tetrakis(3,5-bis(trifluoromethyl)phenyl)borate, bis(trifluoromethane)sulfonamide, and any combination thereof, where the one or more anions $X^-$ counterbalance one or more positive charges in the polymer. For example, one or more anions $X^-$ can be selected from iodide, bromide, chloride, fluoride, hydroxide, carbonate, bicarbonate, and any combination thereof, where the one or more anions $X^-$ counterbalance one or more positive charges in the polymer. In some embodiments, one or more anions $X^-$ is selected from iodide, bromide, chloride, hydroxide, and any combination thereof, where the one or more anions $X^-$ counterbalance one or more positive charges in the polymer. In some embodiments, one or more anions $X^-$ is selected from iodide, hydroxide, and any combination thereof, where the one or more anions $X^-$ counterbalance one or more positive charges in the polymer. For example, for any of the above-described polymers including a repeating unit of Formula (III-A), (III-B), and/or (III-C), the polymer can include one or more hydroxide anions, where the one or more hydroxide anions counterbalance one or more positive charges in the polymer.

The present disclosure further provides a random polymer, including (or consisting essentially of, or consisting of) repeating units of Formula (IV-A), (IV-B), and (IV-C):

(IV-A)

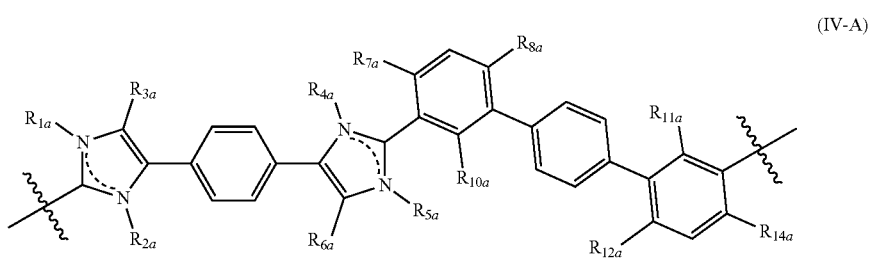

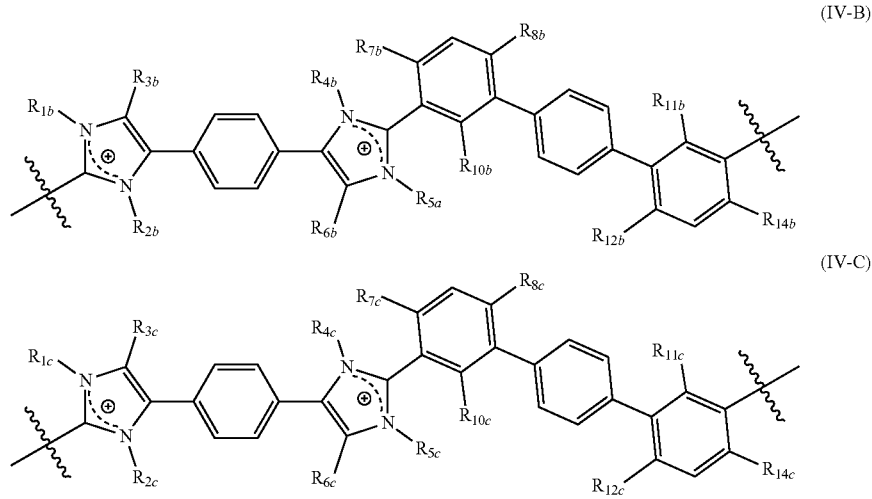

wherein
one of $R_{1a}$ and $R_{2a}$ is absent and the remaining $R_{1a}$ or $R_{2a}$ is selected from alkyl, perfluoroalkyl, heteroalkyl, aryl, and aralkyl;

one of $R_{4a}$ and $R_{5a}$ is absent and the remaining $R_{4a}$ or $R_{5a}$ is selected from alkyl, perfluoroalkyl, heteroalkyl, aryl, and aralkyl;

one of $R_{1b}$, $R_{2b}$, $R_{4b}$, and $R_{5b}$ is absent and the imidazolyl group to which the absent $R_{1b}$, $R_{2b}$, $R_{4b}$, or $R_{5b}$ is connected (i.e., the imidazolyl group where one of its $R_{1b}$, $R_{2b}$, $R_{4b}$, or $R_{5b}$ is absent) is neutral, and the remaining three of $R_{1b}$, $R_{2b}$, $R_{4b}$, and $R_{5b}$ are each independently selected from alkyl, perfluoroalkyl, heteroalkyl, aryl, and aralkyl;

$R_{1c}$, $R_{2c}$, $R_{4c}$, and $R_{5c}$ are each independently selected from alkyl, perfluoroalkyl, heteroalkyl, aryl, and aralkyl;

$R_{3a}$, $R_{6a}$, $R_{3b}$, $R_{6b}$, $R_{3c}$, and $R_{6c}$ are each independently selected from alkyl, perfluoroalkyl, heteroalkyl, aryl, aralkyl, and heteroaryl;

$R_{7a}$, $R_{10a}$, $R_{11a}$, $R_{14a}$, $R_{7b}$, $R_{10b}$, $R_{11b}$, $R_{14b}$, $R_{7c}$, $R_{10c}$, $R_{11c}$, and $R_{14c}$ are each independently selected from alkyl, perfluoroalkyl, and heteroalkyl; and $R_{8a}$, $R_{12a}$, $R_{8b}$, $R_{12b}$, $R_{8c}$, and $R_{12c}$ are each independently selected from hydrogen (H), alkyl, perfluoroalkyl, and heteroalkyl;

wherein the polymer includes m mole percentage repeating units of Formula (IV-A), n mole percentage repeating units of Formula (IV-B), and p mole percentage repeating units of Formula (IV-C), and m is from 0 mole percent to 60 mole percent,
n+p is 40 mole percent to 100 mole percent, and $m+n+p=100\%$.

In some embodiments, for the random polymer including (or consisting essentially of, or consisting of) repeating units of Formula (IV-A), (IV-B), and (IV-C) described above, one of $R_{1a}$ and $R_{2a}$ is absent and the remaining $R_{1a}$ or $R_{2a}$ is selected from methyl and trifluoromethyl; and one of $R_{4a}$ and $R_{5a}$ is absent and the remaining $R_{4a}$ or $R_{5a}$ is selected from methyl and trifluoromethyl.

In some embodiments, for any of the above-described random polymers including (or consisting essentially of, or consisting of) repeating units of Formula (IV-A), (IV-B), and (IV-C), one of $R_{1b}$, $R_{2b}$, $R_{4b}$, and $R_{5b}$ is absent and the imidazolyl group to which the absent $R_{1b}$, $R_{2b}$, $R_{4b}$, or $R_{5b}$ is connected (i.e., the imidazolyl group where one of its $R_{1b}$, $R_{2b}$, $R_{4b}$, or $R_{5b}$ is absent) is neutral, and the remaining three of $R_{1b}$, $R_{2b}$, $R_{4b}$, and $R_{5b}$ are each independently selected from alkyl, perfluoroalkyl, and heteroalkyl. In some embodiments, one of $R_{1b}$, $R_{2b}$, $R_{4b}$, and $R_{5b}$ is absent and the imidazolyl group to which the absent $R_{1b}$, $R_{2b}$, $R_{4b}$, or $R_{5b}$ is connected (i.e., the imidazolyl group where one of its $R_{1b}$, $R_{2b}$, $R_{4b}$, or $R_{5b}$ is absent) is neutral, and the remaining three of $R_{1b}$, $R_{2b}$, $R_{4b}$, and $R_{5b}$ are each independently selected from methyl, and trifluoromethyl.

In some embodiments, for any of the above-described random polymers including (or consisting essentially of, or consisting of) repeating units of Formula (IV-A), (IV-B), and (IV-C), $R_{1c}$, $R_{2c}$, $R_{4c}$, and $R_{5c}$ are each independently selected from alkyl, perfluoroalkyl, and heteroalkyl. For example, $R_{1c}$, $R_{2c}$, $R_{4c}$, and $R_{5c}$ can each be independently selected from methyl and trifluoromethyl. In some embodiments, $R_{1c}$, $R_{2c}$, $R_{4c}$, and $R_{5c}$ are each independently methyl or ethyl. In some embodiments, $R_{1c}$, $R_{2c}$, $R_{4c}$, and $R_{5c}$ are each methyl.

In some embodiments, for any of the above-described random polymers including (or consisting essentially of, or consisting of) repeating units of Formula (IV-A), (IV-B), and (IV-C), $R_{3a}$, $R_{6a}$, $R_{3b}$, $R_{6b}$, $R_{3c}$, and $R_{6c}$ are each independently aryl. For example, $R_{3a}$, $R_{6a}$, $R_{3b}$, $R_{6b}$, $R_{3c}$, and $R_{6c}$ can each independently be phenyl.

In some embodiments, for any of the above-described random polymers including (or consisting essentially of, or consisting of) repeating units of Formula (IV-A), (IV-B), and (IV-C), $R_{7a}$, $R_{10a}$, $R_{11a}$, $R_{14a}$, $R_{7b}$, $R_{10b}$, $R_{11b}$, $R_{14b}$, $R_{7c}$, $R_{10c}$, $R_{11c}$, and $R_{14c}$ are each independently alkyl. For example, $R_{7a}$, $R_{10a}$, $R_{11a}$, $R_{14a}$, $R_{7b}$, $R_{10b}$, $R_{11b}$, $R_{14b}$, $R_{7c}$, $R_{10c}$, $R_{11c}$, and $R_{14c}$ can each independently be methyl or ethyl. For example, $R_{7a}$, $R_{10a}$, $R_{11a}$, $R_{14a}$, $R_{7b}$, $R_{10b}$, $R_{11b}$, $R_{14b}$, $R_{7c}$, $R_{10c}$, $R_{11c}$, and $R_{14c}$ can each independently be methyl.

In some embodiments, for any of the above-described random polymers including (or consisting essentially of, or consisting of) repeating units of Formula (IV-A), (IV-B), and (IV-C), $R_{8a}$, $R_{12a}$, $R_{8b}$, $R_{12b}$, $R_{8c}$, and $R_{12c}$ are each independently alkyl. For example, $R_{8a}$, $R_{12a}$, $R_{8b}$, $R_{12b}$, $R_{8c}$, and $R_{12c}$ can each be independently methyl or ethyl. For example, $R_{8a}$, $R_{12a}$, $R_{8b}$, $R_{12b}$, $R_{8c}$, and $R_{12c}$ can each be independently methyl.

In some embodiments, for any of the above-described random polymers including (or consisting essentially of, or consisting of) repeating units of Formula (IV-A), (IV-B), and (IV-C), n and p are each more than 0 percent.

In some embodiments, for any of the above-described random polymers including (or consisting essentially of, or consisting of) repeating units of Formula (IV-A), (IV-B), and (IV-C), the polymer includes one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof, where the one or more anions $X^-$ counterbalance one or more positive charges in the polymer. For example, the one or more anions $X^-$ can be selected from iodide, bromide, chloride, fluoride, hydroxide, carbonate, bicarbonate, and any combination thereof, where the one or more anions $X^-$ counterbalance one or more positive charges in the polymer. For example, one or more anions $X^-$ can be selected from iodide, bromide, chloride, hydroxide, and any combination thereof, where the one or more anions $X^-$ counterbalance one or more positive charges in the polymer. As another example, one or more anions $X^-$ can be selected from iodide, hydroxide, and any combination thereof, where the one or more anions $X^-$ counterbalance one or more positive charges in the polymer. In some embodiments, for any of the above-mentioned random copolymers including repeating units of Formula (IV-A), (IV-B), and (IV-C), the polymer includes one or more hydroxide anions, where the one or more hydroxide anions counterbalance one or more positive charges in the polymer.

In some embodiments, the present disclosure features an ionic membrane including any of the embodiments of polymers described above.

In certain embodiments, the present disclosure features an ionomer including any of the embodiments of polymers described above. The ionomer can be incorporated into a catalyst layer of a fuel cell, of an electrolyzer, or of other electrochemical devices.

An example of an imidazolium polymer of the present disclosure is provided in Example 1 below. The imidazolium polymer exhibits remarkable hydroxide stability in concentrated caustic solutions at elevated temperatures.

EXAMPLES

Example 1. Synthesis and Characterization of a N-Methylated Imidazolium Polymer A sterically-protected, N-methylated imidazolium polymer that exhibit hydroxide stability in concentrated caustic solutions at 100° C. is provided below.

Reagents and Instruments

Chemicals were purchased from Sigma Aldrich or Combi-Blocks, Inc. and were reagent or ACS grade unless otherwise noted. Glacial acetic acid and potassium iodide were purchased from Caledon Laboratories Ltd. Ethanol (anhydrous) was purchased from Commercial Alcohols. Potassium hydroxide was purchased from Macron Fine Chemicals. Dimethyl sulfoxide (spectrograde), potassium carbonate, potassium chloride, sodium bicarbonate, and hexanes were purchased from ACP Chemicals Inc. Methylene chloride (stabilized), sodium dithionite, acetone, and methanol were purchased from Fisher Scientific. Chloroform and sodium hydroxide were purchased from BDH. Tetrakis(triphenylphosphine)palladium (99%) was purchased from Strem Chemicals. Dimethyl sulfoxide-$d_6$ (99.9%-D), methylene chloride-$d_2$ (99.9%-D), methanol-$d_4$ (99.8%-D) were purchased from Cambridge Isotope Laboratories, Inc. 2,6-dibromobenzaldehyde (3) was prepared according to Lulinski, S.; Serwatowski, J. *J. Org. Chem.* 2003, 68, 5384, incorporated herein by reference in its entirety; 1,4-bis(phenylethynyl)benzene was prepared according to Sonogashira, K.; Tohda, Y.; Hagihara, N. *Tetrahedron Lett.* 1975, 16, 4467, incorporated herein by reference in its entirety; and 1,4-bis(benzoylcarbonyl)benzene (bisbenzil) was prepared according to Yusubov, M. S.; Filimonov, V. D. *Synthesis* 1991, 131, incorporated herein by reference in its entirety. Nuclear magnetic resonance (NMR) spectra were obtained on a 400 or 500 MHz Bruker AVANCE III running IconNMR under Top Spin 2.1. The residual $^1$H NMR solvent peaks for DMSO-$d_6$, CD$_2$Cl$_2$, and CD$_3$OD were set to 2.50 ppm, 5.32 ppm, and 3.31 ppm, respectively. The residual $^{13}$C NMR solvent peaks for CD$_2$Cl$_2$ and CD$_3$OD were set 54.00 ppm and 49.00 ppm, respectively.

Synthesis of 2,4,5-triphenyl-1H-imidazole (2)

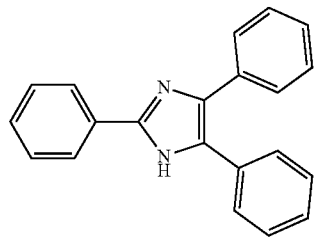

2

Into a 500 mL two-neck round bottom flask was added benzil (12.6 g, 60 mmol), benzaldehyde (6.3 g, 59 mmol), ammonium acetate (45 g, 580 mmol), acetic acid (60 mL), and ethanol (300 mL). The reaction mixture was heated to reflux for 18 h. The reaction mixture was then cooled to room temperature and the solid was collected by filtration. After recrystallization in ethanol, 2 (12.0 g, 69%) was obtained as white crystals. $^1$H NMR (400 MHz, DMSO-$d_6$, ppm) δ: 12.70 (s, 1H), 8.10 (d, J=7.2 Hz, 2H), 7.67-7.07 (m, 13H). $^{13}$C NMR (100 MHz, DMSO-$d_6$, ppm) δ: 145.47, 130.34, 128.65, 128.44, 128.21, 127.74, 127.06, 126.49, 125.17. HRMS (m/z): [M+H]$^+$ calcd for C$_{21}$H$_{17}$N$_2$$^+$, 297.1386; found, 297.1389.

Synthesis of 1,3-dimethyl-2,4,5-triphenyl-1H-imidazolium (HIm) iodide

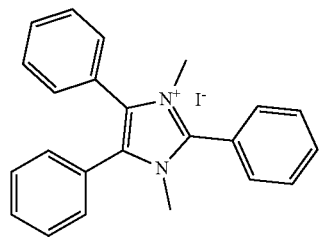

HIm

In a 200 mL round-bottom flask was added powdered potassium hydroxide (1.78 g, 32 mmol) followed by dimethyl sulfoxide (60 mL). The mixture was stirred capped at room temperature for 30 min. A solution of 2 (5.00 g, 16.9 mmol) in dimethyl sulfoxide (60 mL) was then added to the basic solution and stirred for 45 min at room temperature. Iodomethane (1.12 mL, 18.0 mmol) was then added and stirred for 45 min. The mixture was then poured into water (800 mL) containing potassium hydroxide (4.0 g). The resulting precipitate was dissolved in diethyl ether and the organics were collected and washed with water, brine, and water. The organic phase was then dried over magnesium sulfate, filtered, and evaporated at 50° C. using a dynamic vacuum, resulting in the mono-methylated imidazole as a white powder (4.62 g, 88%). Only part of this powder (2.00 g, 6.44 mmol) was further methylated, which was moved into a 50 mL round-bottom flask and dissolved in dichloromethane (15 mL). Iodomethane (1.6 mL, 26 mmol) was added and the capped mixture was stirred for 18 h at 30° C. The solvent was then evaporated at 40° C. using a dynamic vacuum. The resulting solid was triturated in warm diethyl ether and dried under vacuum at 100° C., yielding HIm in iodide form (2.23 g, 77%) as an off-white powder (68% overall yield). $^1$H NMR (500 MHz, DMSO-$d_6$, ppm) δ: 7.98-7.92 (m, 2H), 7.84-7.75 (m, 3H), 7.54-7.45 (m, 10H), 3.54 (s, 6H). $^{13}$C NMR (125 MHz, DMSO-$d_6$, ppm) δ: 144.08, 132.48, 131.25, 130.80, 130.66, 130.07, 129.53, 129.02, 125.53, 121.90, 34.51. HRMS (m/z): [M]$^+$ calcd for $C_{23}H_{21}N_2^+$, 325.1699; found, 325.1708.

Synthesis of 2-mesityl-4,5-diphenyl-1H-imidazole (4)

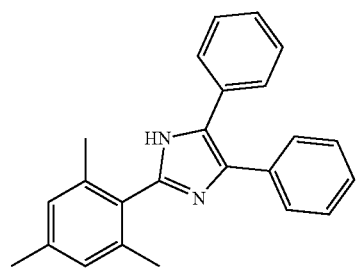

4

In a 50 mL, two-neck round-bottom flask was added benzil (2.1 g, 10 mmol), mesitaldehyde (1.48 mL, 10.0 mmol), ammonium acetate (1.70 g, 22.1 mmol), and monosodium phosphate (0.52 g, 4.3 mmol). The reaction mixture was then stirred at 130° C. for 1 h (the reaction was monitored by TLC). After completion, the mixture was cooled to room temperature and methanol was added. The mixture was filtered to remove insolubles and the filtrate was evaporated under reduced pressure. The crude product was washed with water and hexanes. The solid was recrystallized from acetonitrile twice and dried under vacuum at 80° C. to yield 4 (1.2 g, 36%) as cotton-like fibers. $^1$H NMR (400 MHz, CD$_3$OD, ppm) δ: 7.48 (d, J=7.3 Hz, 4H), 7.38-7.21 (m, 6H), 6.98 (s, 2H), 2.32 (s, 3H), 2.22 (s, 6H). $^{13}$C NMR (100 MHz, CD$_3$OD, ppm) δ: 147.41, 140.32, 139.56, 129.53, 129.10, 129.07, 128.26, 21.29, 20.20. HRMS (m/z): [M+H]$^+$ calcd for $C_{24}H_{23}N_2^+$, 339.1856; found, 339.1862.

Synthesis of 2-mesityl-1,3-dimethyl-4,5-diphenyl-1H-imidazolium (MeIm) iodide

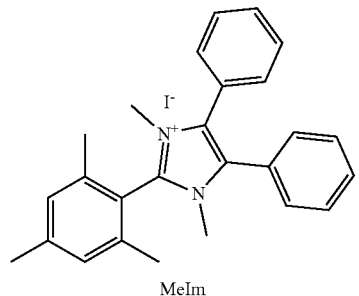

MeIm

Powdered potassium hydroxide (0.1122 g, 2.00 mmol) was added to a 25 mL round-bottom flask. Dimethyl sulfoxide (5 mL) was added and the mixture was vigorously stirred for 30 min. In a separate container, 4 (0.338 g, 1.0 mmol) was dissolved in dimethyl sulfoxide (5 mL). The solution of 4 was then added to the basic solution and the mixture was stirred for 1 h closed at room temperature. Iodomethane (65 μL, 1.04 mmol) was added and the mixture was stirred for 1 h. The mixture was poured into a stirring solution of water (80 mL) containing potassium hydroxide (0.2 g). Diethyl ether (30 mL) was added and stirred until both layers were transparent. The organic layer was decanted and the same process was repeated with additional diethyl ether (2×15 mL). The combined organic layers were washed with water, brine, water. The organic phase was then dried over magnesium sulfate, filtered, and evaporated under dynamic vacuum. Dichloromethane (5 mL) was added to the product and stirred until fully dissolved. Iodomethane (260 μL, 4.2 mmol) was added and the mixture was stirred at 30° C. for 18 h. The solvent was evaporated by dynamic vacuum and diethyl ether (20 mL) was added. The solid was collected by filtration, washed with diethyl ether, and dried under vacuum at 80° C. to obtain MeIm in iodide form (0.31 g, 63%) as off-white flakes. $^1$H NMR (400 MHz, CD$_3$OD, ppm) δ: 7.57-7.43 (m, 10H), 7.26 (s, 2H), 3.53 (s, 6H), 2.44 (s, 3H), 2.24 (s, 6H). $^{13}$C NMR (100 MHz, CD$_3$OD, ppm) δ: 145.19, 140.51, 133.92, 132.09, 131.56, 130.61, 130.25, 126.67, 34.02, 21.46, 19.51. HRMS (m/z): [M]$^+$ calcd for $C_{26}H_{27}N_2^+$, 367.2169; found, 367.2173.

Synthesis of 2-(2,6-dibromophenyl)-4,5-diphenyl-1H-imidazole (6)

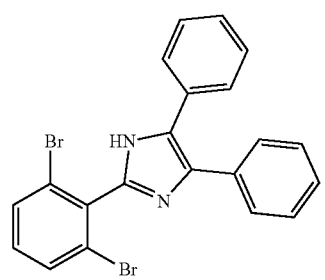

6

In a 1 L, two-neck round-bottom flask was added benzil (10.05 g, 48 mmol), 2,6-dibromobenzaldehyde (13.2 g 50 mmol), ammonium acetate (38.5 g, 500 mmol), acetic acid (50 mL), and ethanol (400 mL). The reaction mixture was heated to reflux for 18 h. The reaction was then cooled to room temperature and poured into water. The precipitate was recrystallized in ethanol/water (250 mL:150 mL) to yield 6 (18.8 g, 86%) as white crystals. $^1$H NMR (400 MHz, CD$_3$OD, ppm) δ: 7.76 (d, J=8.1 Hz, 2H), 7.59-7.41 (m, 4H), 7.40-7.21 (m, 7H). $^{13}$C NMR (100 MHz, CD$_3$OD, ppm) δ: 144.48, 133.91, 132.08, 131.59, 128.17, 127.74, 125.68. HRMS (m/z): [M+H]+ calcd for C$_{21}$H$_{15}$Br$_2$N$_2$$^+$, 452.9597; found, 452.9603.

Synthesis of 2-(2,6-dibromophenyl)-1-methyl-4,5-diphenyl-1H-imidazole (7)

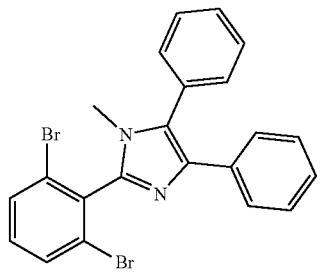

7

To a round-bottom flask with a stopper was added potassium hydroxide (0.4062 g, 7.24 mmol) and dimethyl sulfoxide (24 mL). The mixture was allowed to stir at room temperature for 30 min. Compound 6 (0.90 g, 2.0 mmol) was then added as well as additional dimethyl sulfoxide (4.0 mL). This mixture was stirred at room temperature for 45 min. Iodomethane (160 µL, 2.6 mmol) was added and the mixture was stirred at room temperature for an additional 45 min. The reaction was slowly poured into water. The precipitate was collected by filtration and vacuum dried to yield 7 (0.8581 g, 92%) as a white powder. $^1$H NMR (500 MHz, DMSO-d$_6$, ppm) δ: 7.87 (d, J=8.1 Hz, 2H), 7.59-7.49 (m, 3H), 7.49-7.39 (m, 5H), 7.21 (t, J=7.6 Hz, 2H), 7.14 (t, J=7.3 Hz, 1H), 3.17 (s, 3H). $^{13}$C NMR (125 MHz, DMSO-d$_6$, ppm) δ: 144.95, 136.14, 134.50, 133.15, 133.03, 131.94, 130.63, 130.35, 129.26, 128.92, 128.81, 128.10, 126.23, 126.01, 125.81, 31.13. HRMS (m/z): [M+H]$^+$ calcd for C$_{22}$H$_{17}$Br$_2$N$_2$$^+$, 466.9753; found, 466.9756.

Synthesis of 2-([1,1':3',1''-terphenyl]-2'-yl)-1-methyl-4,5-diphenyl-1H-imidazole (8)

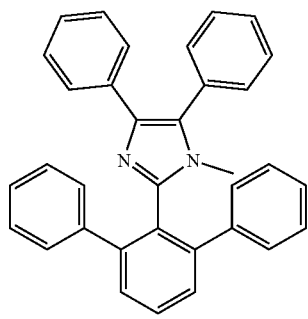

8

In a 250 mL round-bottom flask was added 7 (4.0002 g, 8.54 mmol), benzeneboronic acid (3.1225 g, 25.6 mmol), 1,4-dioxane (120 mL), and 2 M K$_2$CO$_{3\,(aq.)}$ (40 mL). The mixture was bubbled with argon for 5 min and then tetrakis (triphenylphosphine)palladium (0) (104 mg, 0.090 mmol) was added. The mixture was heated to 104° C. for 18 h. The resulting mixture was bubbled with air for 15 min until the solution became black and the mixture was cooled to room temperature while stirring. Ethyl acetate was added and the organic phase was washed with water and brine. After drying over magnesium sulfate, the solvent was evaporated under dynamic vacuum. The resulting material was dissolved in dichloromethane and flushed through a celite/silica pad with dichloromethane and ethyl acetate. The filtrate was evaporated and the solid was washed with hexanes. The solid was recrystallized twice with ethyl acetate/hexanes, washed with hexanes, and dried under vacuum at 100° C. to yield 8 (1.44 g, 36%) as white powder. $^1$H NMR (500 MHz, DMSO-d$_6$, ppm) δ: 7.76-7.68 (m, 1H), 7.59 (d, J=7.7 Hz, 2H), 7.46-7.39 (m, 3H), 7.36-7.25 (m, 6H), 7.25-7.18 (m, 3H), 7.19-7.13 (m, 2H), 7.10 (t, J=7.4 Hz, 2H), 7.07-7.02 (m, 1H), 6.99 (dd, J=7.4, 2.0 Hz, 2H), 2.60 (s, 3H). $^{13}$C NMR (125 MHz, DMSO-d$_6$, ppm) δ: 144.50, 143.19, 140.41, 135.76, 134.90, 130.74, 130.31, 130.02, 129.03, 128.99, 128.60, 128.57, 128.16, 127.95, 127.87, 126.97, 125.89, 125.81, 30.91. HRMS (m/z): [M+H]$^+$ calcd for C$_{34}$H$_{27}$N$_2$$^+$, 463.2169; found, 463.2176.

Synthesis of 2-([1.1':3',1''-terphenyl]-2'-yl)-1,3-dimethyl-4,5-diphenyl-1H-imidazolium (PhIm) iodide

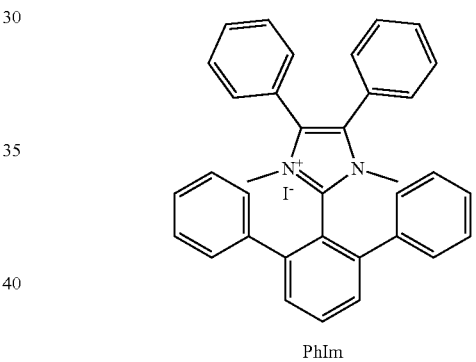

PhIm

In a 25 mL round-bottom flask was added 8 (0.8009 g, 1.73 mmol) and dichloromethane (8.0 mL). After complete dissolution, iodomethane (0.54 mL, 8.67 mmol) was added and the capped mixture was heated at 30° C. for 18 h. The solvent was removed at 40° C. under dynamic vacuum and the resulting solid was washed with diethyl ether. Drying the solid at 80° C. under vacuum yielded PhIm in iodide form (0.94 g, 90%) as off-white powder. $^1$H NMR (500 MHz, DMSO-d$_6$, ppm) δ: 8.07 (t, J=7.8 Hz, 1H), 7.89 (d, J=7.8 Hz, 2H), 7.59-7.49 (m, 6H), 7.49-7.39 (m, 6H), 7.33-7.24 (m, 4H), 7.11-7.03 (m, 4H), 3.04 (s, 6H). $^{13}$C NMR (125 MHz, DMSO-d$_6$, ppm) δ: 144.15, 143.38, 138.05, 133.97, 131.63, 130.41, 130.32, 129.95, 129.11, 129.09, 128.59, 128.26, 124.41, 118.30, 33.63. HRMS (m/z): [M]$^+$ calcd for C$_{35}$H$_{29}$N$_2$$^+$, 477.2325; found, 477.2334.

Scheme 2 below summarizes the reactions for making HIm, MeIm, and PhIm. The first reaction is the condensation of an aldehyde with benzil in the presence of excess ammonium acetate to yield imidazole-derivatives (36-86%). Deprotonation and methylation of 2 and 4 produced HIm (68%) and MeIm (63%), respectively. Partial methylation of 6 to produce 7 (92%) allowed for the Suzuki-Miyaura coupling of 7 with phenylboronic acid to produce 8 (36%). Methylation of 8 resulted in the model compound PhIm (90%).

Scheme 2. Synthetic route used to prepare the imidazolium small molecule compounds HIm, MeIm, and PhIm.

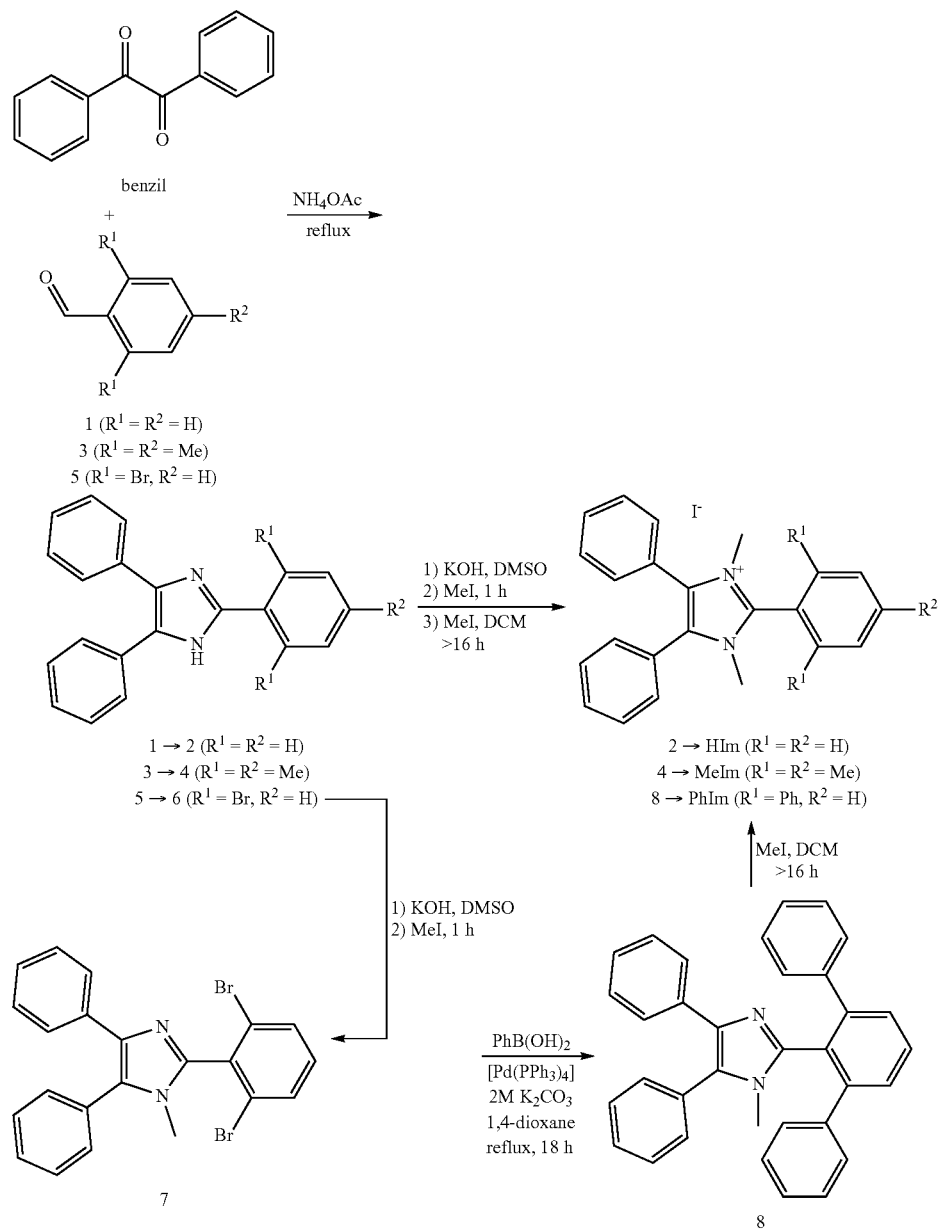

Synthesis of 3-bromo-2,4,6-trimethylbenzaldehyde (9)

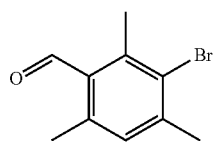

Mesitaldehyde (14.8 g, 0.10 mol) was dissolved in 200 mL of glacial acetic acid. A separate solution containing bromine (16.0 g, 0.10 mol) in 60 mL of glacial acetic acid was then added and the resulting mixture was stirred for 2 h at 50° C. The solution was then slowly poured into 1.5 L of stirring distilled water and stirred for 2 h. The precipitate was filtered and washed with water twice. The crude product was recrystallized in ethanol/water (140 mL:60 mL) twice. The crystals were collected and dried under vacuum at 60° C. overnight, yielding 9 (16.4 g, 72%) as a white powder. $^1$H NMR (400 MHz, CD$_3$OD, ppm) δ: 10.48 (s, 1H), 7.08 (s, 1H), 2.64 (s, 3H), 2.47 (s, 3H), 2.41 (s, 3H). $^{13}$C NMR (100 MHz, CD$_3$OD, ppm) δ: 194.88, 144.80, 141.11, 140.65, 133.86, 132.80, 127.96, 24.78, 20.10, 19.90. HRMS (m/z): [M+H]$^+$ calcd for C$_{10}$H$_{12}$BrO$^+$, 227.0066; found, 227.0056.

Synthesis of 2,2''',4,4''',6,6'''-hexamethyl-p-terphenyl-3,3'''-dicarbaldehyde (10)

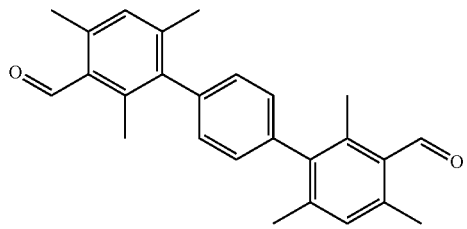

In an argon-purged 100 mL round-bottom flask with a stirbar and condenser was added 9 (2.26 g, 10 mmol), 1,4-phenylenediboronic acid (0.83 g, 5 mmol), 1,4-dioxane (50 mL), 2 M $K_2CO_3$ (16 mL), and aliquat 336 (1 drop). The mixture was bubbled with argon for 20 min and tetrakis(triphenylphosphine)palladium(0) (0.02 g, 0.2 mol %) was added. After refluxing for 22 h under argon, the solution was cooled to 80° C. and poured into a stirring, 55° C. solution of ethanol (80 mL)-water (100 mL). The mixture was slowly cooled to room temperature and the resulting precipitate was filtered. The solid was purified by flash column chromatography using chloroform as the eluent. The collected solid was dried under vacuum at 80° C., yielding 10 (5.15 g, 58%) as a white powder. $^1$H NMR (400 MHz, $CD_2Cl_2$, ppm) δ: 10.63 (d, J=1.0 Hz, 2H), 7.19 (s, 4H), 7.07 (s, 2H), 2.60 (s, 6H), 2.34 (s, 3H), 2.32 (s, 3H), 2.09 (s, 3H), 2.07 (s, 3H). $^{13}$C NMR (100 MHz, $CD_2Cl_2$, ppm) δ: 194.34, 142.57, 142.54, 141.75, 140.23, 140.21, 139.48, 139.45, 139.43, 131.67, 131.47, 131.46, 130.17, 21.88, 21.82, 20.88, 20.86, 17.80, 17.77. HRMS (m/z): $[M+H]^+$ calcd for $C_{26}H_{27}O_2^+$, 371.2006; found, 371.2006.

Polymer Synthesis

HMT-PPI (see, FIG. 2A) was prepared using a modified generalized microwave-assisted polymerization method, described for example in Chauveau, E. et al., *Polymer* 2008, 49, 5209, and Chauveau, E. et al.; *Polymer* 2014, 55, 6435, each of which is herein incorporated in its entirety. Specifically, bisbenzil (0.34 g, 1.0 mmol), 10 (0.37 g, 1.0 mmol), ammonium acetate (1.54 g, 20.0 mmol), glacial acetic acid (3.0 mL), and 1,4-dioxane (9.0 mL) were added to a high-pressure glass reactor and microwave-irradiated at 120° C. for 35 min. Once the reaction mixture was cooled to room temperature, it was poured into chloroform to precipitate the polymer. The polymer was collected and broken into smaller pieces. The solid was dissolved in dimethyl sulfoxide and re-precipitated into chloroform. The collected solid was washed with acetone and water and dried under vacuum at 80° C. to yield HMT-PPI (0.66 g, 98%) as a light yellow fiber. $^1$H NMR (400 MHz, DMSO-$d_6$, ppm) δ: 7.68-7.54 (m, 4H), 7.34 (s, 4H), 7.21 (s, 4H), 7.16-7.04 (m, 4H), 7.00-6.82 (m, 4H), 2.21 (s, 6H), 2.12-1.73 (m, 12H). The $^1$H NMR spectrum of HMT-PPI was taken by heating HMT-PPI in DMSO-$d_6$ with two drops of 40 wt % NaOD (in $D_2O$) until fully dissolved.

Polymer Functionalization

Into a 50 mL round-bottom flask with stir bar and glass stopper was added HMT-PPI (0.336 g, 0.5 mmol), 5 M $KOH_{aq}$ (0.3 mL), and dimethyl sulfoxide (8 mL). The mixture was heated to 70° C. in air. Additional dimethyl sulfoxide (2 mL) was added followed by 5 M $KOH_{aq}$ (0.2 mL) while at 70° C. After 30 min, the mixture was cooled to room temperature. While vigorously stirring the solution, iodomethane (68 μL, 1.1 mmol) was rapidly added and stirred for 30 min, resulting in precipitate. The mixture was poured into 150 mL of stirring water and the solid was collected and washed with water. The solid was stirred in 150 mL of water containing potassium iodide (0.5 g) at room temperature for 2 h. The solid was collected and washed with water twice. The solid was dried under vacuum at 80° C. The polymer was then transferred into a 25 mL round-bottom flask with stir bar and glass stopper followed by dichloromethane (10 mL) to dissolve the partially-methylated polymer. Excess iodomethane (200 μL, 3.2 mmol) was added and the mixture was heated to 30° C. for 20 h. The solvent was evaporated under reduced pressure and the polymer was vacuum dried at 80° C. to yield HMT-PMPI (see, FIG. 2A) in iodide form (0.47 g, 95%) as a stiff, yellowish fibrous solid. GPC analysis, $M_n$=49,900 g $mol^{-1}$, $M_w$=66,900 g $mol^{-1}$, $M_w/M_n$=1.39. $^1$H NMR (400 MHz, DMSO-$d_6$, ppm) δ: 7.67 (s, 4H), 7.58-7.22 (m, 16H), 3.55 (d, J=12.7 Hz, 12H), 2.25 (s, 6H), 2.15 (s, 6H), 1.93 (s, 6H). The $^1$H NMR spectrum of HMT-PMPI was taken after casting and washing with water.

Size-Exclusion Chromatography

The size-exclusion chromatography analyses were obtained by using Water HPLC HR 5, HR 4 and HR 3 columns with HPLC grade DMF (containing 0.10 M LiBr) as eluent. Polystyrene samples were purchased from Waters Associates Inc., were used as standards for the calibration.

Casting Procedure

The HMT-PMPI polymer in iodide form was dissolved in 5 mL of hot dimethyl sulfoxide, filtered into a flat Petri dish, and allowed to slowly dry at 86° C. for at least 24 h in air. The film was peeled off the glass and transferred into deionized water for at least 24 h before the ion exchange steps. The films produced by this method were transparent yellow and were approximately 25 microns thick.

Solution Degradation Test

The stability of HIm, MeIm, PhIm, and tetramethyl ammonium (TMA) were evaluated using a degradation test, described in Wright, A. G. et al., *Angew. Chem. Int. Ed.* 2016, 55, 4818, herein incorporated by reference in its entirety. A solution of the model compound (0.02 M) was prepared by dissolving the model compound (iodide form) in 3 M NaOD with $CD_3OD/D_2O$ (7:3 $CD_3OD:D_2O$ by mass, unless otherwise specified). The $CD_3OD$ used here as a good solvent for reagents and products, thus enabling NMR spectroscopic analysis to be carried out. The mixture was heated to 80° C. in a closed PTFE vial for up to 240 h. At specific times, samples were extracted for $^1$H NMR spectroscopic analysis.

The degradation of MeIm and PhIm was quantified using Equation 1:

$$\text{Relative Imidazolium Remaing (\%)} = 100 \left( \frac{1 - \frac{nx_t}{y_t}}{1 - \frac{nx_0}{y_0}} \right) \quad (1)$$

For PhIm, $x_t$ is the integration value for the 7.73-7.66 ppm region (representing 1H of the de-methylated PhIm degradation product) relative to the integration of the total aromatic region of 8.10-6.70 ppm at time t, represented as $y_t$ ($x_0$ and $y_0$ are $x_t$ and $y_t$ at time 0 h, respectively). For MeIm, $x_t$ is the integration value for the 6.98-6.94 ppm region (representing 2H of the de-methylated MeIm degradation product) relative to the integration of the total aromatic region of 7.70-6.90 ppm at time t, represented as $y_t$·n represents the relative proton ratio of the y region to that of the x region (ie., for PhIm and MeIm, n is $$\frac{23}{1} \text{ and } \frac{12}{2},$$

respectively).

The degradation of HIm was quantified using Equation 2:

$$\text{Relative Imidazolium Remaing (\%)} = 100\left(\frac{\frac{w_t}{z_t}}{\frac{w_0}{z_0}}\right) \quad (2)$$

where $w_t$ is the integration value for the 7.92-7.83 ppm region (representing 2H of the starting material HIm) relative to the integration of the total aromatic region of 8.11-7.02 ppm at time t, represented as $z_t$ ($w_0$ and $z_0$ are $w_t$ and $z_t$ at time 0 h, respectively).

The degradation of benzyltrimethyl ammonium (BTMA) was quantified using Equation 3:

$$\text{Relative Imidazolium Remaing (\%)} = 100\left(\frac{\frac{x_t}{y_t}}{\frac{x_0}{y_0}}\right) \quad (3)$$

where $x_t$ is the integration value for the 7.65-7.45 ppm region (representing 5H of the starting material BTMA) relative to the integration of the total aromatic region of 7.65-7.18 ppm at time t, represented as $y_t$ ($x_0$ and $y_0$ are $x_t$ and $y_t$ at time 0 h, respectively).

The degradation of cetyltrimethyl ammonium (CTAB) was quantified using Equation 4

$$\text{Relative Imidazolium Remaing (\%)} = 100\left(\frac{x_t}{x_0}\right) \quad (4)$$

where $x_t$ is the integration value for the 3.38-3.32 ppm region (representing 2H of the starting material HIm) relative to the integration of 0.88-0.77 ppm at time t, set as 3 H ($x_0$ is $x_t$ at time 0 h).

The degradation of tetramethyl ammonium (TMA) was quantified using Equation 5:

$$\text{Relative Ammonium Remaing (\%)} = 100\left(\frac{M_0 + 1.5 \times M_1}{(M_0 + 1.5 \times M_1) + (N_0 + 1.5 \times N_1) \times 4/3}\right) \quad (5)$$

Where $M_0$ is the integration value for the 3.28-3.24 ppm region (representing 12 H of the starting material TMA), $M_1$ is the integration value for the 3.24-3.20 ppm region (representing 2 H of the starting material TMA which was deuterium-exchanged). $N_0$ is the integration value for the 2.20-2.17 ppm region (representing 9 H of the degraded product trimethyl amine), $N_1$ is the integration value for the 2.17-2.15 ppm region (representing 2 H of the degraded product trimethyl amine which was deuterium-exchanged).

After the previously mentioned 240 h degradation test, the solution was cooled to room temperature. The organic degradation products were then isolated using the following method: The mixture was poured into a beaker, using water to wash out any remaining solution into the beaker. The mixture was acidified with dilute, aqueous hydrochloric acid until the pH was neutral. Diethyl ether was added and the organic layer was washed with water three times, dried over magnesium sulfate, filtered, and evaporated at 40° C. using a dynamic vacuum. The resulting residue was then analyzed by mass spectrometry. For the varying $CD_3OD:D_2O$ degradation tests of MeIm, the $^1H$ NMR integration areas were appropriately adjusted to accommodate the relative peak shifts resulting from the change in solvent.

Powder Degradation Test

For compound MeIm, degradation tests were performed in 3, 5, 7, and 10 M $NaOD/D_2O$. The model compound (0.02 M) was dispersed in base solution inside PTFE containers and then heated in an oven at 80° C. for 240 h. Afterwards, the samples were filtered, washed with 4 mL $D_2O$ and directly dissolved in $CD_3OD$ for $^1H$ NMR spectroscopic analysis. The spectra were all baseline-corrected using the "Full Auto (Polynomial Fit)" function found in MestReNova.

Membrane Degradation Test

HMT-PMPI membranes were initially converted from as-cast iodide form into chloride form by soaking the membranes in 1 M $NaCl_{aq}$ for 48 h (exchanging the solution with fresh 1 M NaCl half-way through) and then washed with deionized water over 48 h with multiple fresh exchanges. The membrane was then subjected to 1, 2, 5, 7, and 10 M $NaOH_{aq}$ in closed glass containers at 80, 90, and 100° C. for 7 days, respectively. The membranes were then exchanged back to chloride form by repeating the 1 M $NaCl_{aq}$ soak (48 h) and water wash (48 h) as previously described. After drying the membranes, they were dissolved in DMSO-$d_6$ for $^1H$ NMR spectroscopic analysis.

Ionic Conductivity

Membrane pieces of HMT-PMPI were initially soaked in 1 M $NaOH_{aq}$ for 48 h at room temperature (with one fresh exchange half-way through) followed by washing with deionized water over 48 h with multiple fresh exchanges at room temperature in air. The mixed hydroxide/bicarbonate/carbonate ionic resistance of the membrane was measured in the in-plane direction using a two-point probe by electrochemical impedance spectroscopy. The HMT-PMPI in its chloride form was obtained by the same way instead by soaking in 1 M $NaCl_{aq}$. Specifically, an AC potential was applied over a frequency range of 100-$10^7$ Hz with a Solartron SI 1260 impedance/gain-phase analyser at room temperature and in water. The membrane charge transfer resistance (R), determined from a best fit of a standard Randles circuit to the measured Nyquist plot, was used to calculate the ionic conductivity (σ) with Equation 6:

$$\sigma = \frac{l}{AR} \quad (6)$$

where l is the distance between the two electrodes and A is the cross-sectional area of the membrane.

Water Uptake

The membrane was exchanged to the mixed hydroxide/bicarbonate/carbonate form and chloride form as described in the previous ionic conductivity section. The hydrated membrane was then taken out of the deionized water solution, pressed between Kimwipes to remove any excess water on the surface, and weighed immediately ($W_w$). The wet membrane was then dried under vacuum at 40° C. until a constant dry weight was obtained ($W_d$). The water uptake ($W_u$) was for three samples using Equation 7 and the standard deviation was used as the error.

$$W_u = \frac{W_w - W_d}{W_d} \quad (7)$$

Mechanical Strength

The membranes were die-cut to a barbell shape using a standard ASTM D638-4 cutter. The mechanical properties of the membranes were measured under ambient conditions on a single column system (Instron 3344 Series) using a crosshead speed of 5 mm min$^{-1}$. The determined tensile strength and elongation at break were averaged over three samples. The error reported is the standard deviation.

DFT Calculations

Structures along the degradation pathways of HIm, MeIm, and PhIm were performed using B3LYP density functional theory (DFT) under Gaussian G09, as described, for example in Frisch, M. J. et al. Gaussian-09 Revision D.01 (Gaussian Inc. Wallingford Conn., 2009), incorporated herein by reference in its entirety. The Polarizable Continuum Model (PCM) implemented in G09 used an Integral Equation Formalism (IEFPCM) with water as solvent ($\varepsilon$=78.36). All structures were pre-optimized using 6-31G(d) basis set and refined with 6-311++G(2d,2p) basis set, tight convergence criteria and no symmetry. Reagents, intermediates (IS) and products (P) were optimized to an energy minimum. Transition states (TS) were optimized using Berny algorithm, having one imaginary frequency, and were confirmed by calculating the intrinsic reaction coordinate (IRC). Frequency analysis for 298.15 K was performed to obtain reaction free energy ($\Delta G$) and reaction free energy of activation ($\Delta G^\ddagger$). Values are given with respect to the sum of the reagent free energy: imidazolium cation+2 OH$^-$ for the ring-opening reaction and imidazolium cation+OH$^-$ for the de-methylation reaction. The Supporting Information contains the coordinates of the reagents and all determined transition state structures along the degradation reaction pathways.

Single Crystal X-Ray Diffraction (XRD)

X-ray data was collected on a Bruker Smart instrument equipped with an APEX II CCD area detector fixed at a distance of 5.0 cm from the crystal and a Cu Kα fine focus sealed tube (1.54178 Å) operated at 1.5 kW (50 kV, 30 mA), filtered with a graphite monochromator. Data was collected at ambient conditions. All diffraction data were processed with the Bruker Apex II software suite. The structures were solved with direct methods (SIR92) and subsequent refinements were performed using ShelXle, as described, for example, in Hübschle, C. B. et al., B. J. Appl. Crystallogr. 2011, 44, 1281, incorporated herein by reference in its entirety. MeIm was crystallized from water in iodide form.

Incorporation into AEMFCs

Catalyst ink was formed by dropwise addition of a 5 wt % dispersion of iodide-form HMT-PMPI in MeOH into a rapidly stirred slurry of Pt/C catalyst in a water-methanol solution. In the final catalyst ink, the solvent ratio was 3:1 MeOH:H$_2$O, solids comprised 1 wt %, and ionomer comprised 15 wt % of solids with Pt/C electrocatalyst comprising the balance. As an electrocatalyst for the homopolymer direct membrane deposition cell, a commercial 10 wt % Pt/C was used. Catalyst ink was coated onto a heated substrate (70° C., Sigracet 24BC gas-diffusion layer) by ultrasonicating spray coater (Sono-Tek Exactacoat SC) to a loading of 0.5 mg Pt/cm$^2$, to form gas-diffusion electrodes (GDEs). To form direct membrane deposition (DMD) type fuel cells, a 2.5 wt % solution of iodide-form HMT-PMPI in MeOH was sprayed onto the GDEs to a thickness of 10 μm by weight (i.e. a total membrane thickness of 20 μm when constructed), in an analogous method as described in Vierrath, S. et al., Power Sources, 2016, 326, 170-175, incorporated herein by reference in its entirety. An in-depth comparison of these FC constructions is available in Klingele, M. et al., Electrochem. Comm., 2016, 70, 65-68, incorporated herein by reference. All components were soaked 24 to 48 h in 6 M KOH.

Operation as AEMFCs

The resultant DMDs were gasketed to ensure 20-30% compression of the GDL and compressed to 3.4 N·m (30 in·lbs) in a fuel cell hardware to form AEMFCs. Test stations with heated humidifiers and circuit-interrupt systems for continuous measurement of membrane/ionomer resistance (iR) were employed (Teledyne Medusa RD 890CL, Scribner Associates). FCs were heated to the given temperature and conditioned by a single slow current ramp to maintain 0.4-0.5 V until a stable potential was achieved.

Electrochemical Analysis of AEMFCs

In situ hydroxide conductivity of the membrane ($\sigma_{OH^-}$) was determined from the membrane thickness, L (cm), cross-sectional area of the membrane, A (cm$^2$), and measured membrane/ionomer resistance in the Ohmic region using Equation 8:

$$\sigma_{OH^-} = \frac{L}{R_M A} \quad (8)$$

Error analysis accounted for both iR data and membrane thickness. This is a standard method in our group, conservative and consistent with standard reference membranes such as Nafion 211 and 212 as described, for example in Skalski, T. J. G.; Britton, B.; Peckham, T. J.; Holdcroft, S. *J. Am. Chem. Soc.*, 2015, 137, 12223-12226 and Adamski, M. et al., *Angew. Chem. Intl. Ed.*, 2017, 56, each of which is incorporated herein in its entirety.

Stability and Degradation Characteristics

Figure 1B:
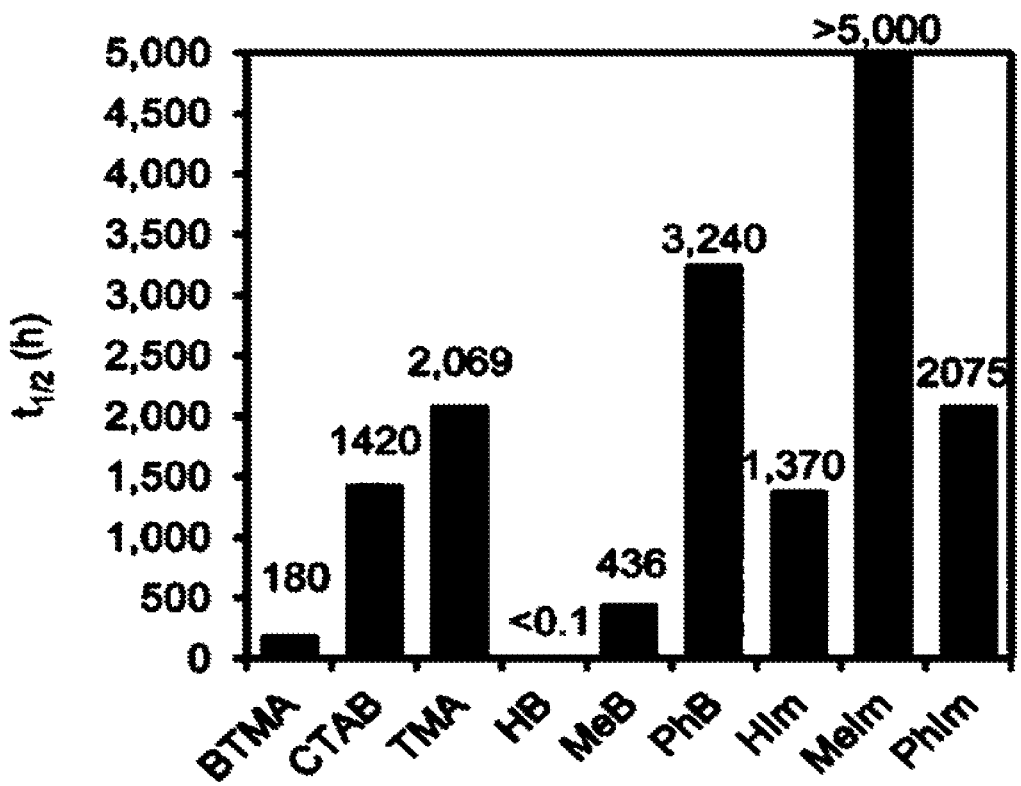
FIG. 1B is a graph of the half-lives ($t_{1/2}$) of embodiments of ammoniums, benzimidazoliums, and imidazoliums dissolved at a concentration of 0.02 M in a 3 M NaOD solution containing 70 wt % $CD_3OD$ in $D_2O$ at 80° C.
Figure 1C:
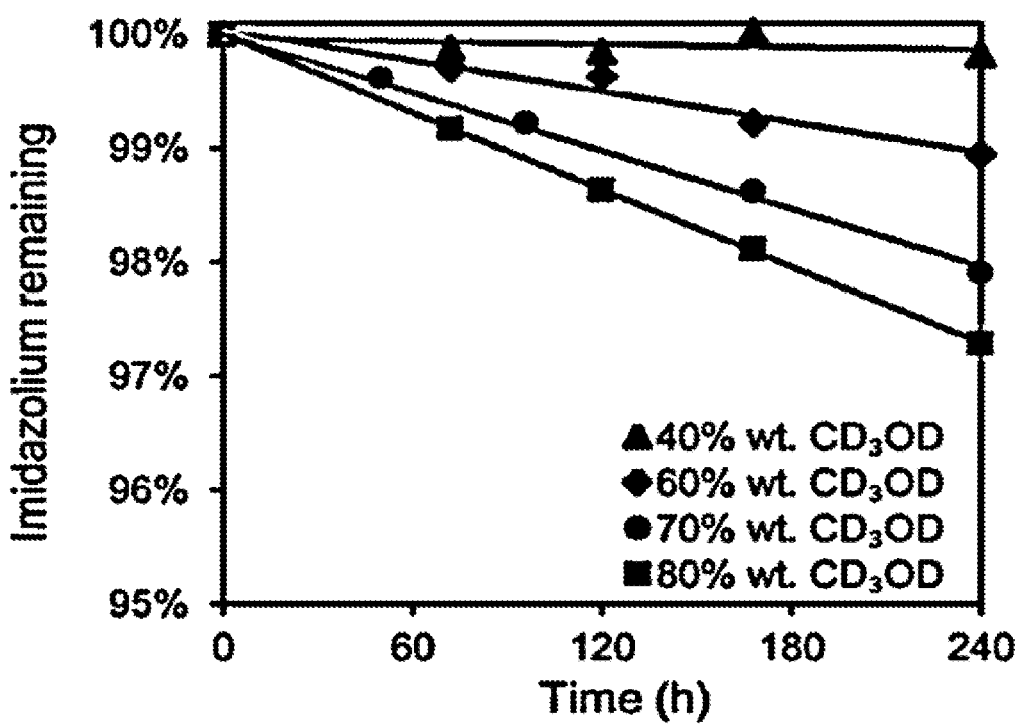
FIG. 1C is a graph showing the extent of degradation of an embodiment of a small molecule (MeIm) in 3 M NaOD at 80° C. in varying $CD_3OD:D_2O$ wt % concentrations (c) over time.
Figure 1D:
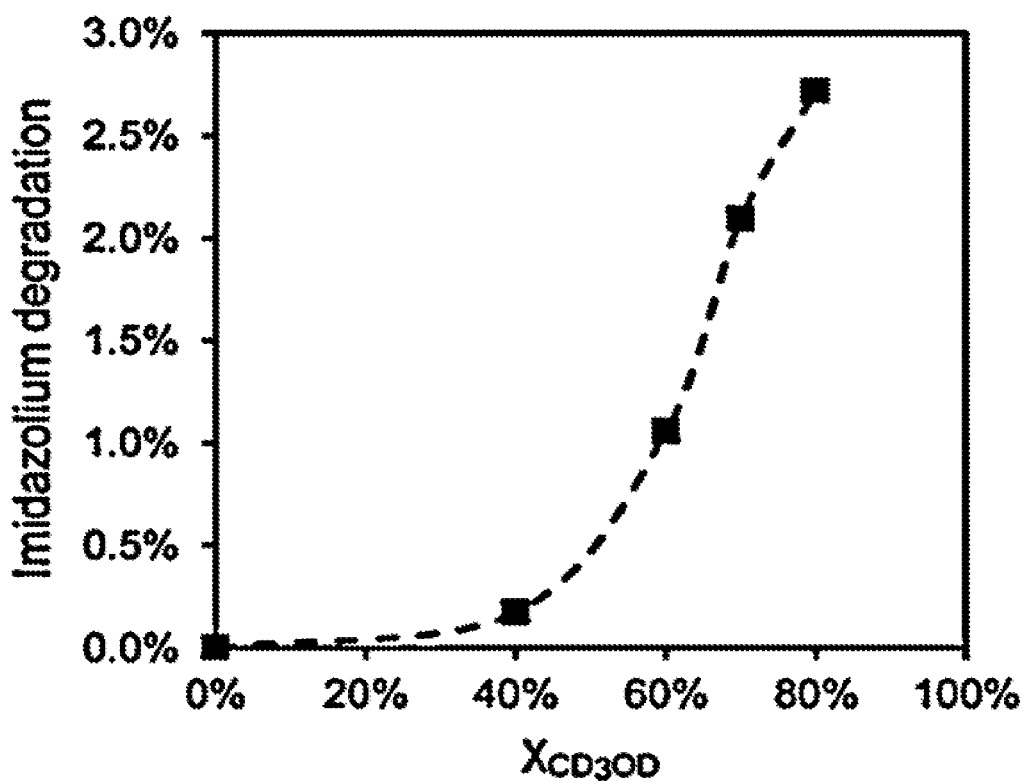
FIG. 1D is a graph showing the extent of degradation of an embodiment of a small molecule (MeIm) in 3 M NaOD at 80° C. in varying $CD_3OD:D_2O$ wt % concentrations after 240 h.
Figure 1E:
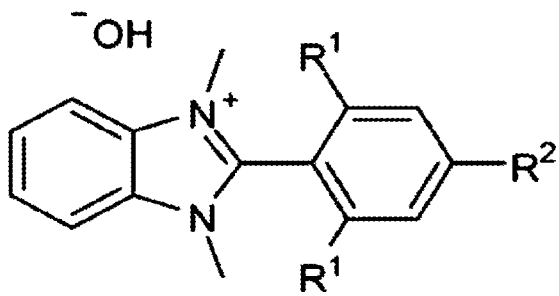
FIG. 1E shows the chemical structures of embodiments of ammoniums, benzimidazoliums, and imidazoliums.
Figure 1E:
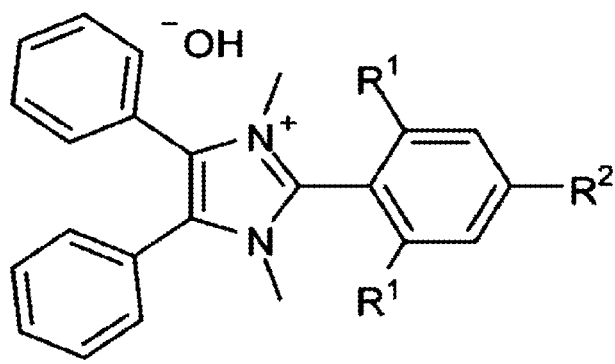
Figure 5A:
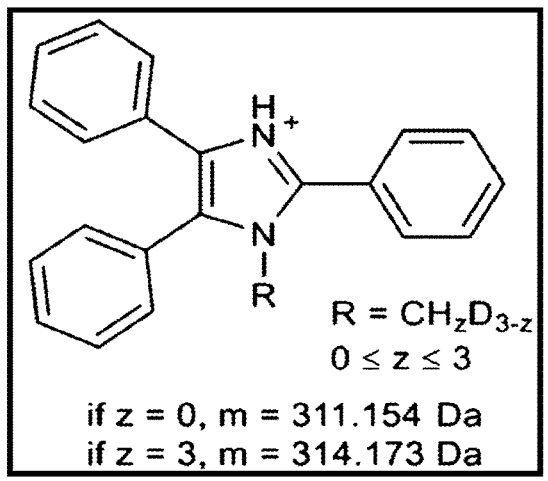
FIG. 5A shows the structure of an embodiment of a degradation product (e.g., a de-methylated degradation product) of an embodiment of imidazolium small molecule (HIm).
Figure 5B:
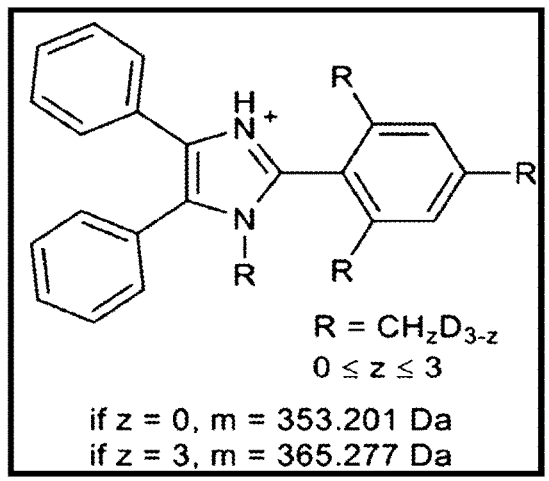
FIG. 5B shows the structure of an embodiment of a degradation product (e.g., a de-methylated degradation product) of an embodiment of imidazolium small molecule (MeIm).
Figure 5C:
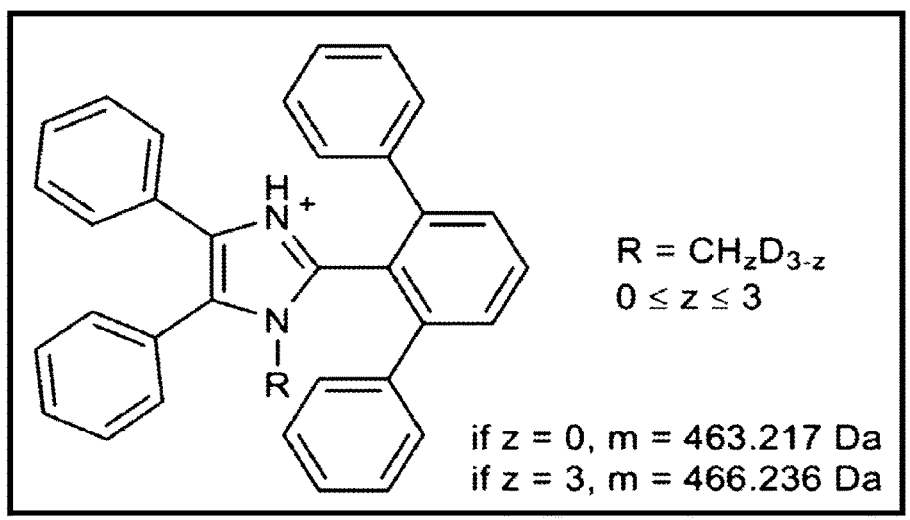
FIG. 5C shows the structure of an embodiment of degradation product (e.g., a demethylated degradation product) of an embodiment of imidazolium small molecule (PhIm).

The extent of degradation was quantified in caustic solutions, and the degradation pathways were identified, for three imidazolium cations, which possessed ortho-hydrogen (HIm), methyl (MeIm), and phenyl (PhIm) groups attached to the C2-phenyl (chemical structures shown in FIG. 1E). These model compounds were synthesized through intermediate compounds 1-8 as discussed above. The percentage of each model compound remaining in 3 M NaOD/CD$_3$OD/D$_2$O (7:3 wt. CD$_3$OD:D$_2$O) at 80° C. as a function of time is shown in FIG. 1A. After 240 h at 80° C., 88%, 98%, and 93% of HIm, MeIm, and PhIm, respectively, remained in solution. According to $^1$H NMR spectroscopy and mass spectrometry, MeIm and PhIm cations decomposed via de-methylation of the N-methyl group (FIGS. 5B and 5C). The degradation pathway of HIm was more complex, with additional products observed due to ring-opening (FIG. 5A). By fitting the rate of degradation to an exponential function, signifying pseudo-first order degradation, the half-lives ($t_{1/2}$) of the compounds were calculated. For comparison, various t-alkylammonium cations, and benzimidazolium cations (see Wright, A. G. et al., S. *Angew. Chem. Int. Ed.* 2016, 55, 4818, incorporated herein by reference in its entirety) were also evaluated under the same conditions (FIG. 1B). The most stable of these model compounds was MeIm which exhibited $t_{1/2}$ of >5000 h, much higher than the benchmark t-alkylammonium TMA and BTMA cations (2069 h and 180 h), and benzimidazolium cation MeB and PhB (436 h and 3240 h).

It was observed that the rate of degradation is dependent on the weight fraction of $CD_3OD$ in $D_2O$ ($\chi CD_3OD$), as shown in FIGS. 1C and 1D. Decreasing the amount of deuterated methanol resulted in a decreased rate of degradation for MeIm. Without wishing to be bound by theory, it is believed that methanol is often used in "aqueous" degradation experiments as it is a solvent for reagents and products, thus enabling NMR spectroscopic analysis to be carried out. However, it is misleading to use methanol in aqueous degradation studies, as methanol may change the degradation pathway. MeIm was therefore heated in aqueous solutions of 3, 5, 7, and 10 M NaOD at 80° C. and 100° C. for 240 h. No degradation was observed by NMR spectroscopy (<1% experimental error).

Figure 2A:
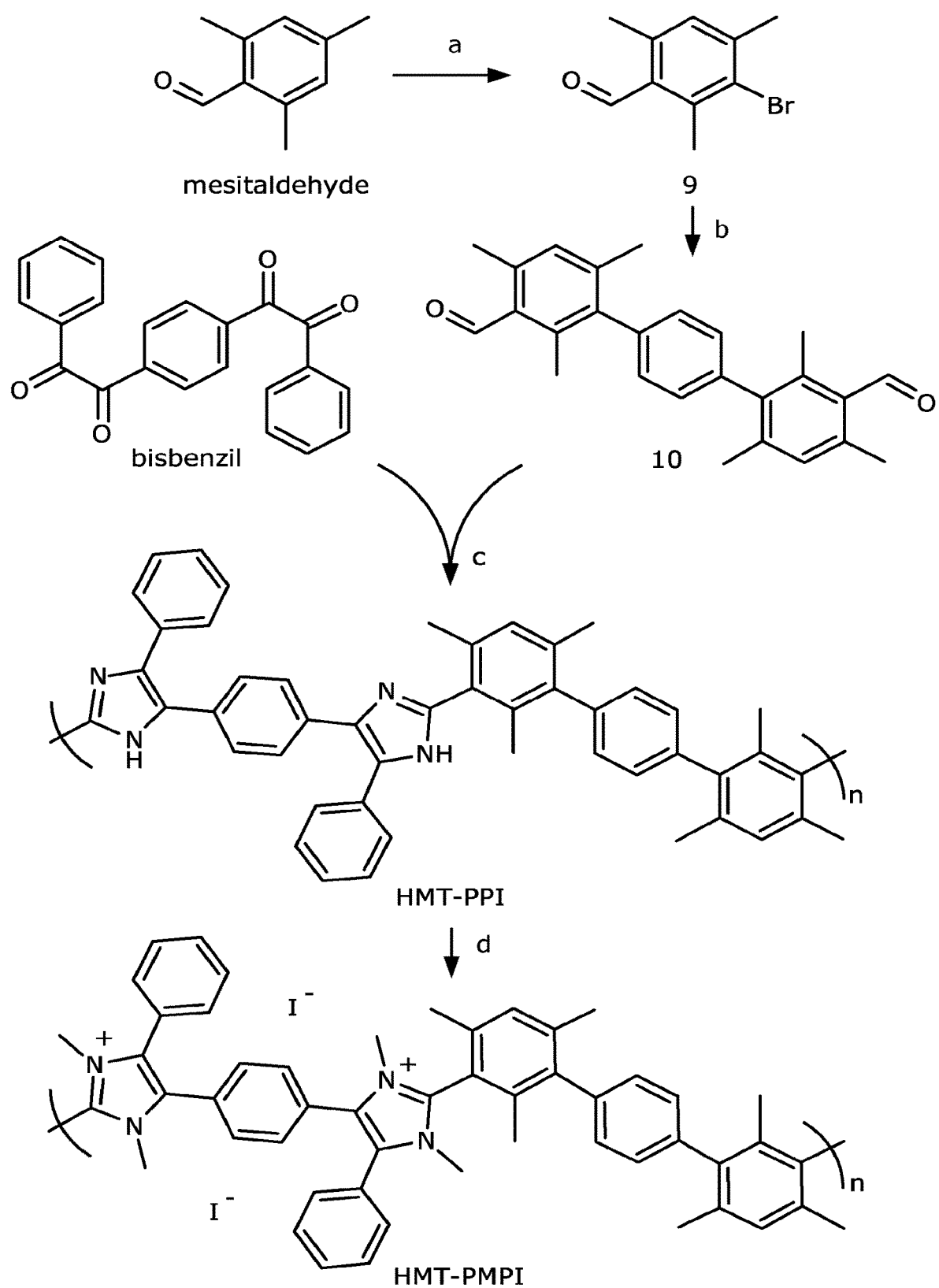
FIG. 2A is a scheme showing the synthesis of an embodiment of a polymer of the present disclosure (e.g., poly (arylene-imidazolium) HMT-PMPI), where in steps a and b, Compound 10 was prepared by bromination of mesitaldehyde to produce 9 (a, 72%) followed by Suzuki-Miyaura coupling of 9 with 1,4-phenylenediboronic acid to yield 10 (b, 58%). In steps c and d, microwave polycondensation of monomer 10 with bisbenzil in the presence of excess ammonium acetate provided poly(arylene-imidazole) HMT-PPI (c, 98%), which was deprotonated and subsequently methylated to produce poly(arylene-imidazolium) HMT-PMPI (d, 95%) in iodide form.
Figure 2B:
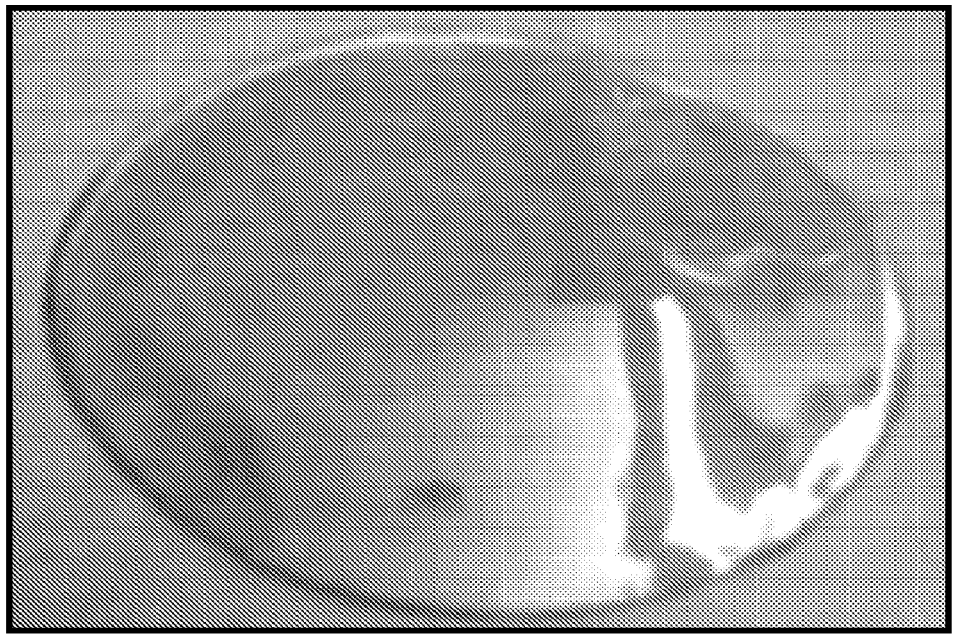
FIG. 2B is a photograph of a circular-cast membrane including an embodiment of a polymer of the present disclosure (HMT-PMPI).
Figure 2C:
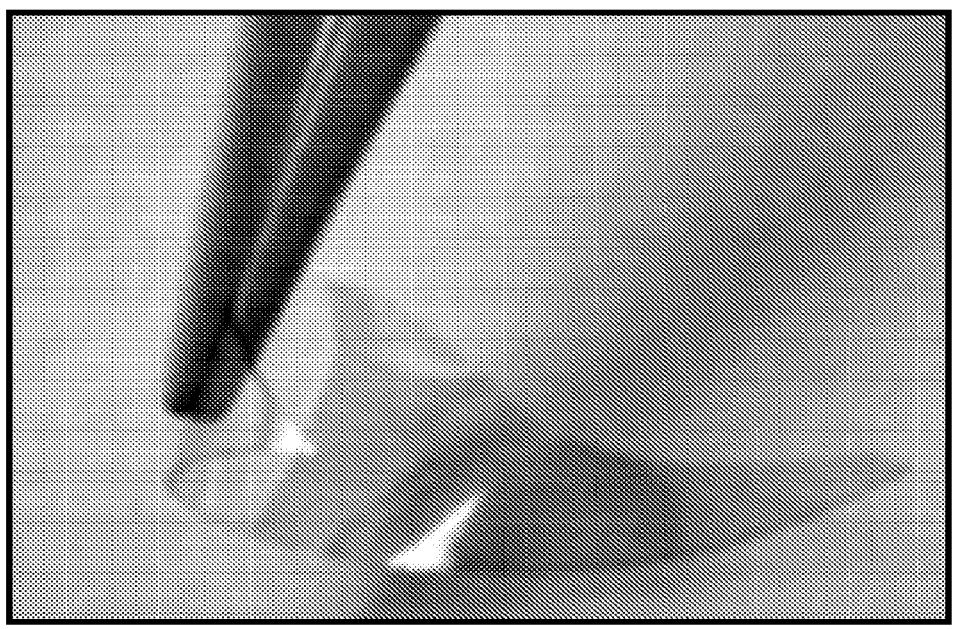
FIG. 2C is a photograph of a piece cut from the membrane of FIG. 2B.
Figure 2D:
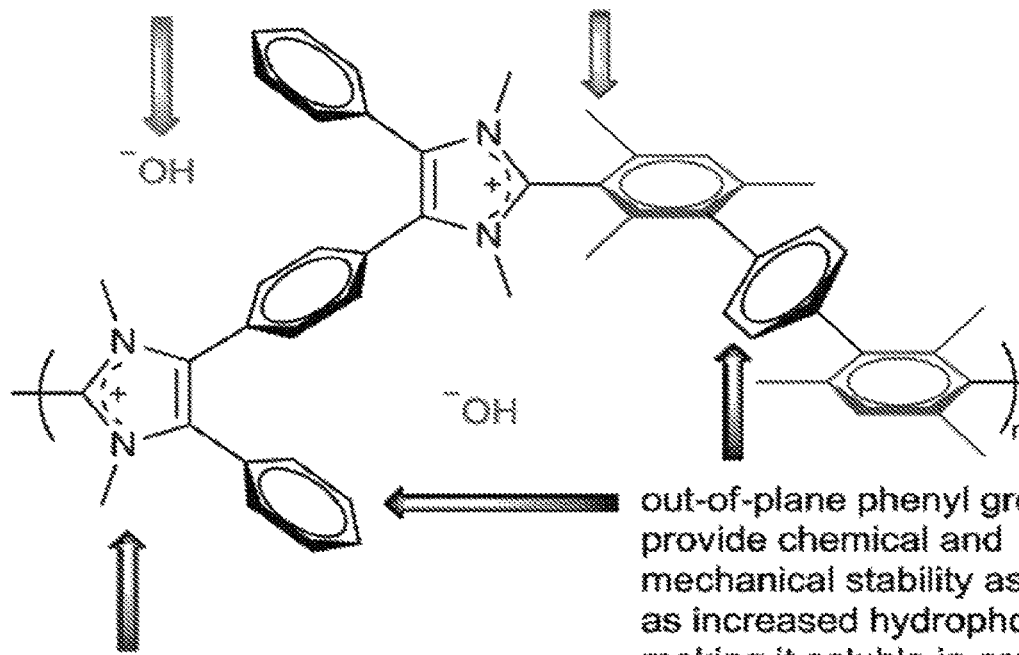
FIG. 2D is a chemical structure of an embodiment of a polymer of the present disclosure.
Figure 3:
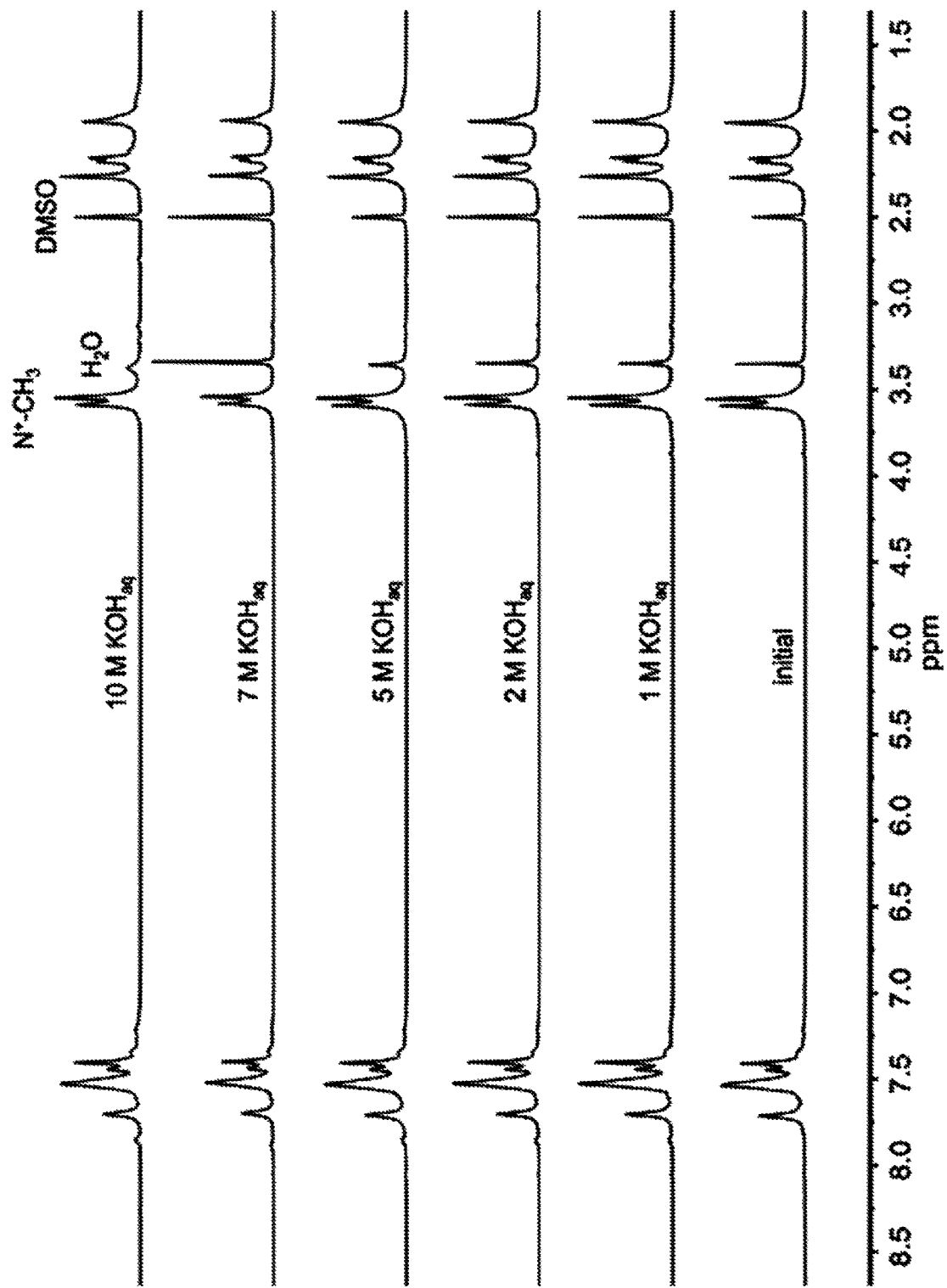
FIG. 3 shows the $^1H$ NMR spectra of an embodiment of a polymer of the present disclosure, specifically HMT-PMPI in chloride form in DMSO-d6, after immersion of membranes containing HMT-PMPI in varying concentrations of $KOH_{(aq)}$ at 100° C. for 168 h. No chemical degradation of HMT-PMPI occurred.
Figure 6:
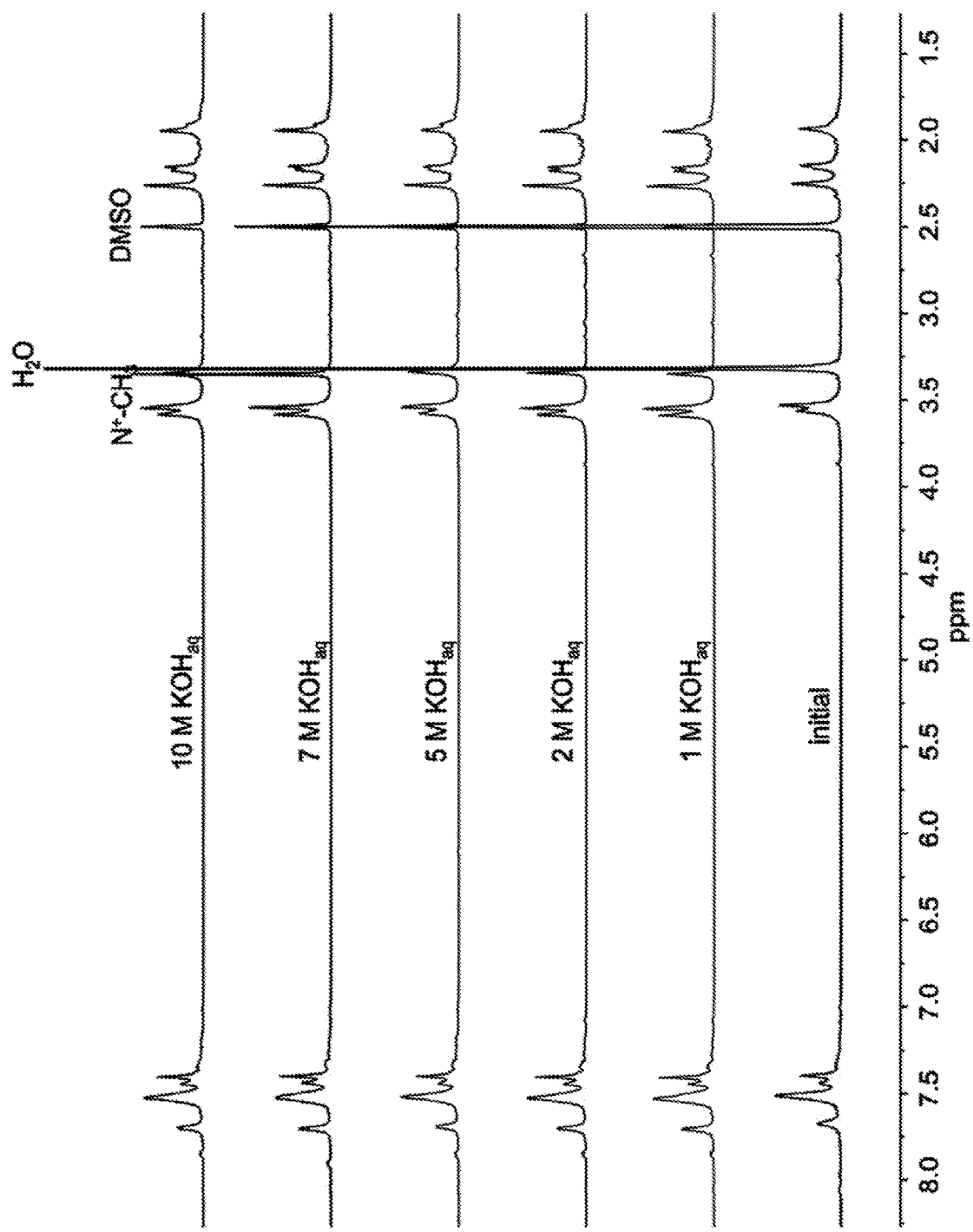
FIG. 6 shows $^1$H NMR spectra of an embodiment of a polymer of the present disclosure (HMT-PMPI in chloride form dissolved in DMSO-$d_6$ after immersion of membranes in varying concentrations of $KOH_{aq}$ at 80° C. for 168 h), where no obvious chemical degradation of the polymer occurred under these harsh conditions.

As MeIm was found to exhibit the highest stability in highly caustic solutions, poly(arylene-imidazolium) HMT-PMPI was designed that incorporates the same o-methyl architecture, as shown in FIG. 2A. The polymer backbone poly(arylene-imidazole) HMT-PPI was prepared by microwave-assisted polycondensation of dialdehyde 10 with bis-benzil. Subsequent deprotonation and alkylation produced the desired methyl-protected poly(arylene-imidazolium) (HMT-PMPI) with 67 kg mol$^{-1}$ Mw and 1.39 PDI, which was cast from DMSO into tough, pliable, transparent yellow films (FIGS. 2B and 2C) with 43.5±1.4 MPa tensile strength and 44.3±9.6% elongation at break. After conversion of the membrane into its hydroxide form HMT-PMPI possessed an ion exchange capacity (IEC) of 2.61 meq g$^{-1}$. In its fully hydrated state, it exhibited an air-equilibrated ion conductivity of 14 mS cm$^{-1}$ at 25° C. and 82±5 wt. % water uptake, the latter representing 18 $H_2O$ per ion pair. The air-equilibrated, OH$^-$ form of the polyelectrolyte membrane was insoluble in water at 25° C. but slowly dissolved in pure water above 80° C. The polymer may be rendered insoluble by reducing the IEC, as previously shown for HMT-PMBI. See, e.g., Wright, A. G. Holdcroft, S. *ACS Macro Lett.* 2014, 3, 444; Wright, A. G et al., *Energy Environ. Sci.* 2016, 9, 2130; and Thomas, O. D. et al.; *Polym. Chem.* 2011, 2, 1641; and Weissbach, et al., T.; Wright, A. G.; Peckham, T. J.; Alavijeh, A. S.; Pan, V.; Kjeang, E.; Holdcroft, S. Chem. Mater. 2016, 28, 8060.21. Li, N.; Leng, The polymer was insoluble at 80° C. in basic solutions above pH 13. The stability of AEMs to caustic solutions is typically measured by their immersion in aqueous hydroxide solutions at elevated temperature for extended periods. This procedure usually results in non-first-order degradation rates due to the heterogeneity of the experiment, wherein the degradation occurs rapidly at the beginning of the experiment (within ~100 h). When thin films (25 μm) of HMT-PMPI were immersed in 1, 2, 5, 7, and 10 M $KOH_{aq}$ heated to 80, 90, and 100° C. for 7 days (168 h), no degradation of the polymer was observed by $^1$H NMR spectroscopy, as shown, for example, in FIGS. 3 and 6. To the extent that the lifetimes can be calculated, HMT-PMPI exhibits a half-life>5000 h in 10 M $KOH_{aq}$ at 100° C.

Figure 4A:
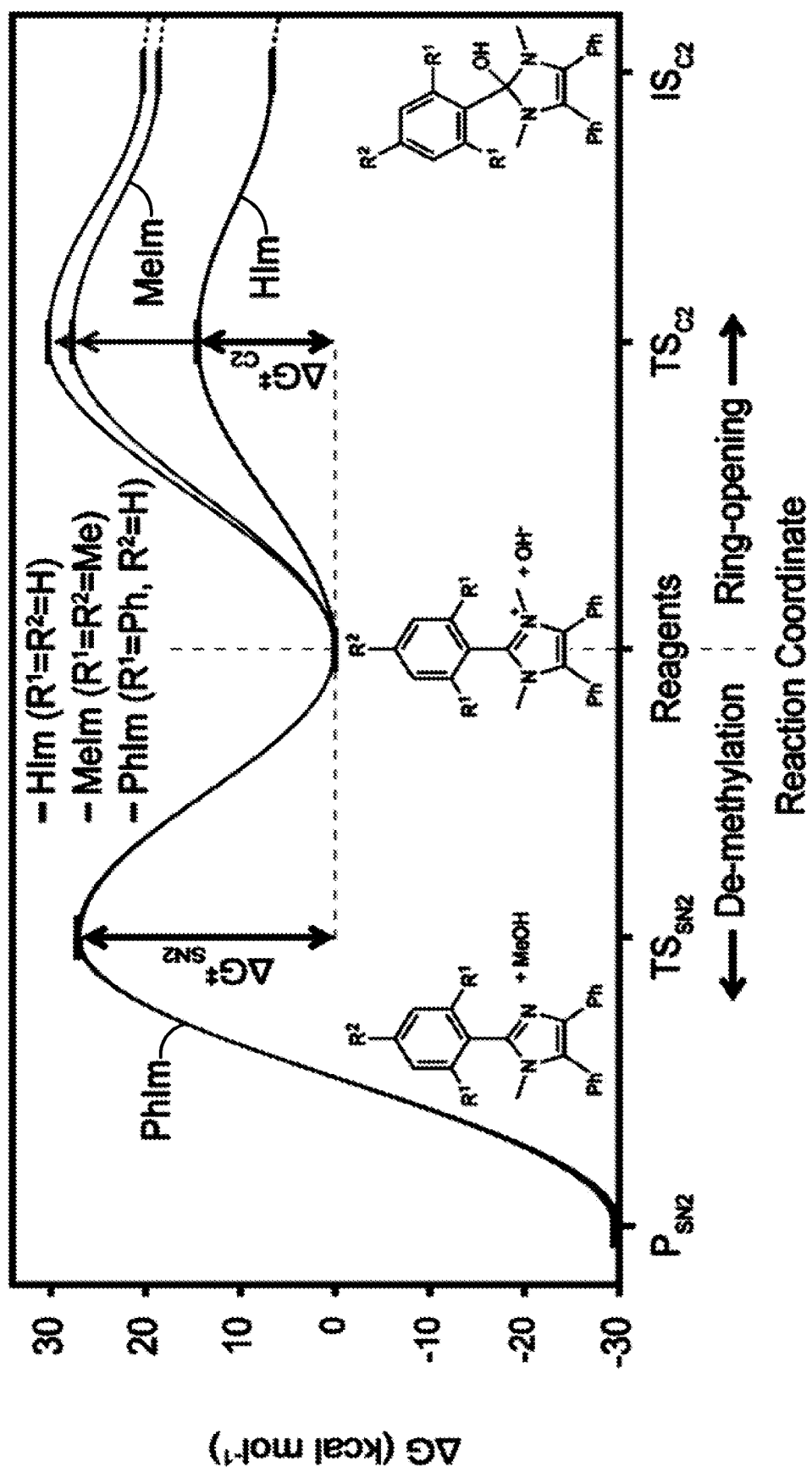
FIG. 4A shows a density functional theory (DFT)-calculated reaction profiles of embodiments of imidazolium small molecules. The free energies (ΔG) for reagents, transition states (TS), intermediate states (IS), and products (P) were optimized for three imidazolium hydroxides, which have hydrogen-, methyl-, or phenyl-groups ortho to the C2-position (HIm, MeIm, and PhIm, respectively, as reagents), along a de-methylation pathway or a ring-opening pathway. Water was used as the solvent and was optimized at 298.15 K.
Figure 4B:
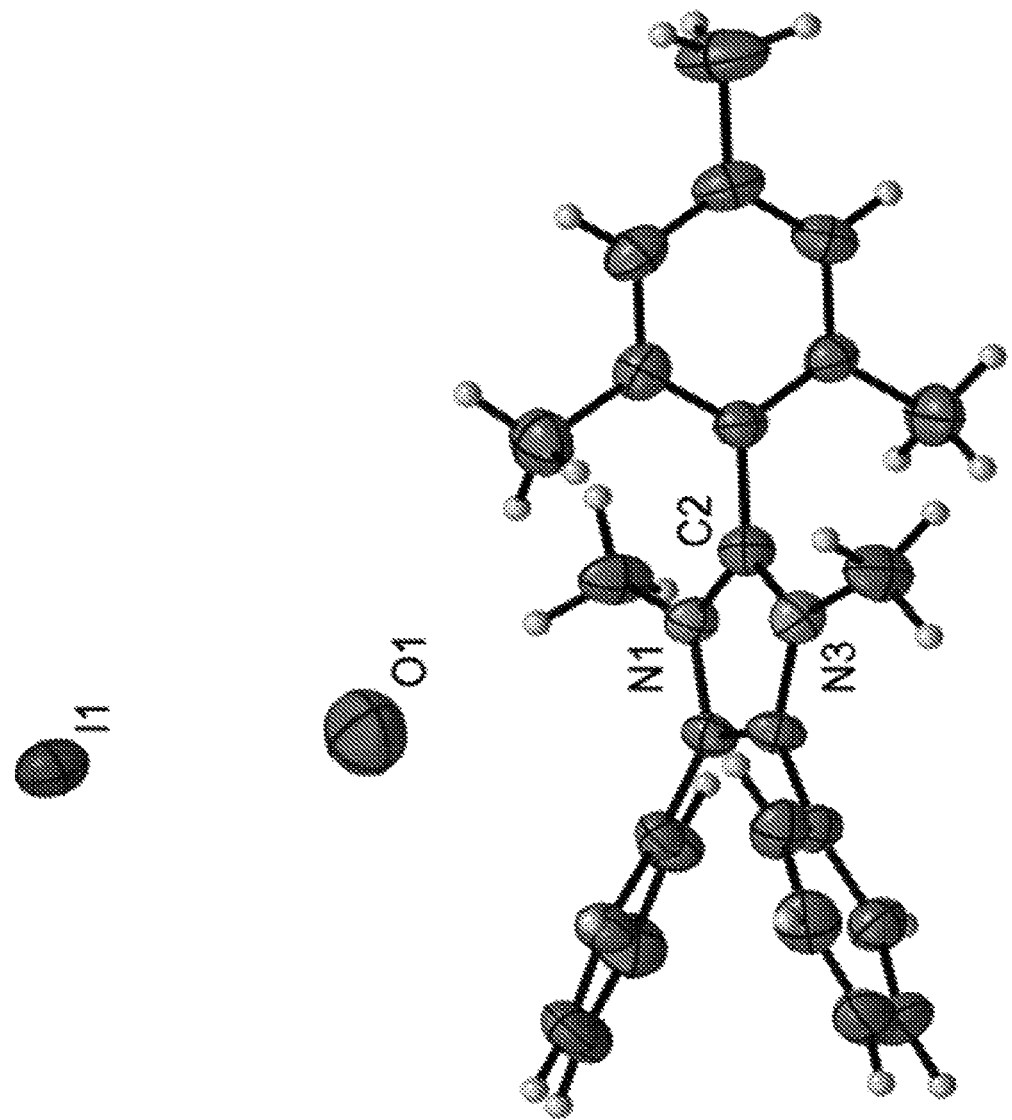
FIG. 4B is a single crystal x-ray diffraction (XRD) structure of an embodiment of an imidazolium small molecule (MeIm in iodide form with co-crystallized $H_2O$ (hydrogens not shown) possessing thermal ellipsoids) shown at a 50% probability level.
Figure 7:
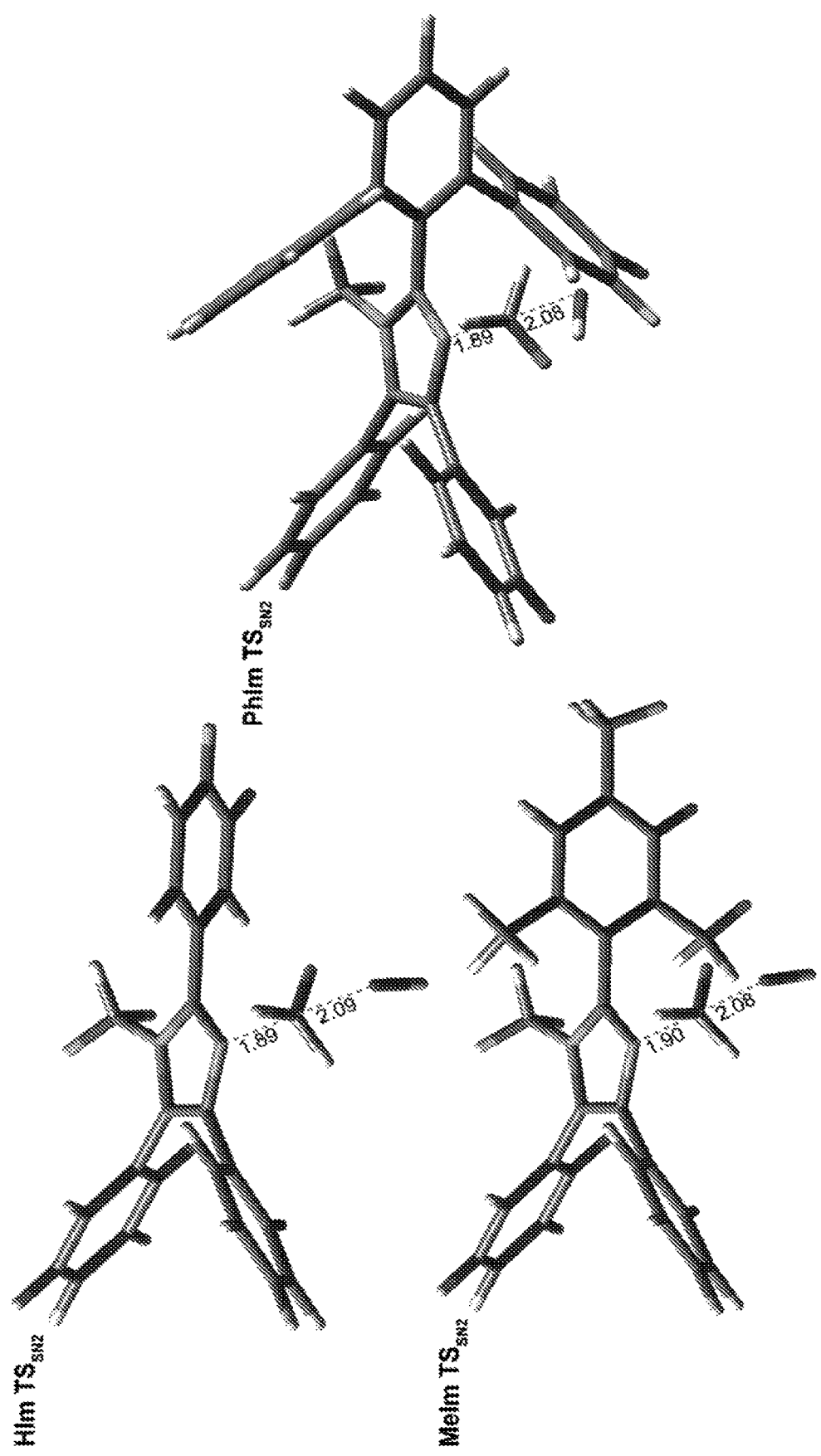
FIG. 7 shows chemical structures of the de-methylation transition state for embodiments of model imidazolium hydroxides. The transition states of the de-methylation degradation reaction ($TS_{SN2}$) of HIm, MeIm, and PhIm by hydroxide were optimized using B3LYP DFT calculations at 298.15 K in water. The distances (Å) of the de-methylated carbon to both the nitrogen and hydroxyl oxygen are labeled.
Figure 8:
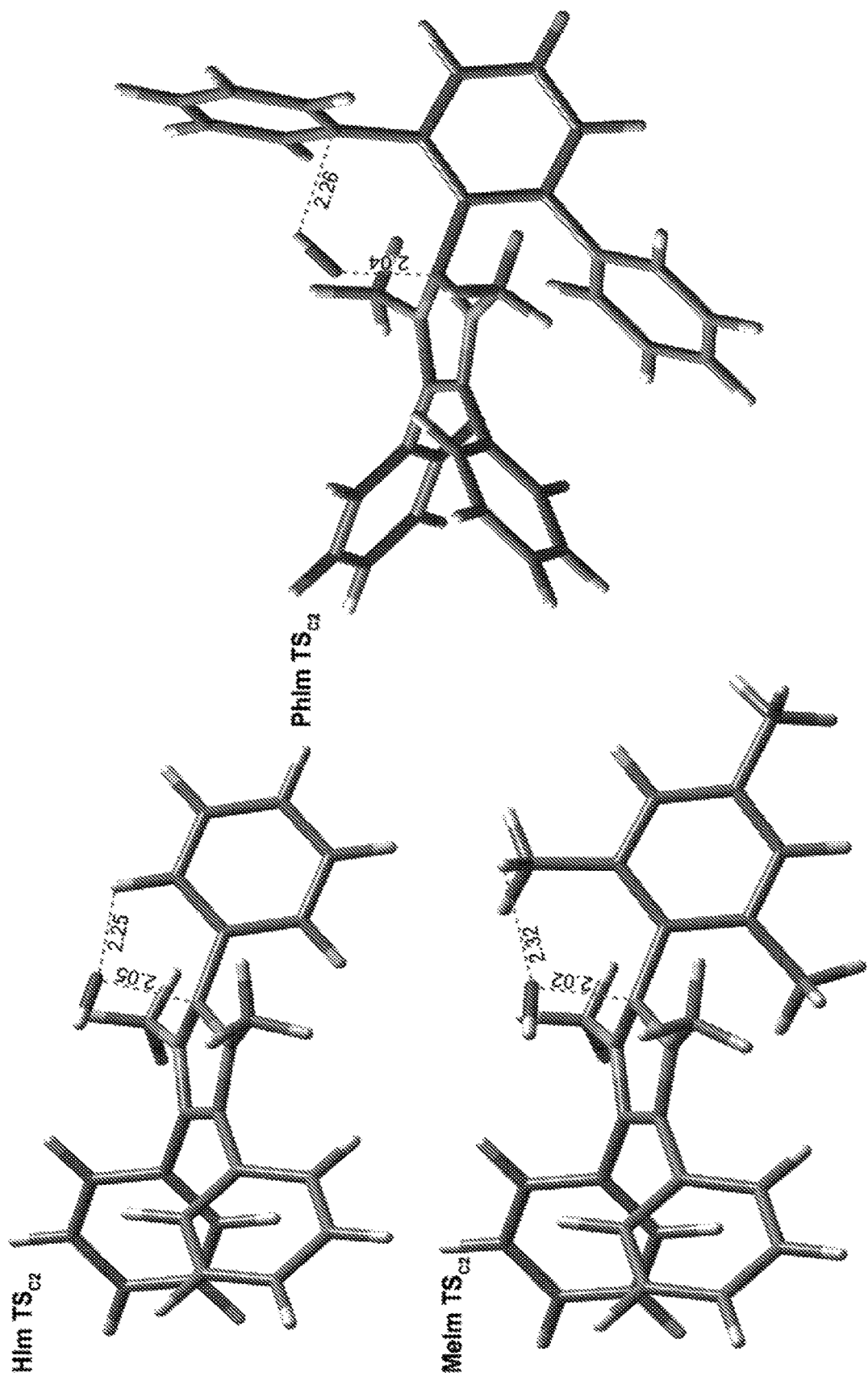
FIG. 8 shows chemical structures of the first transition state for the ring-opening degradation of embodiments of small molecule imidazolium hydroxides. The transition state of the ring-opening reaction ($TS_{C2}$) of HIm, MeIm, and PhIm were optimized using B3LYP DFT calculations at 298.15 K in water. The distance (Å) of the C2-position of the imidazolium to the hydroxyl oxygen atom and the distance between the hydroxide to the steric protecting group are labeled.
Figure 9:
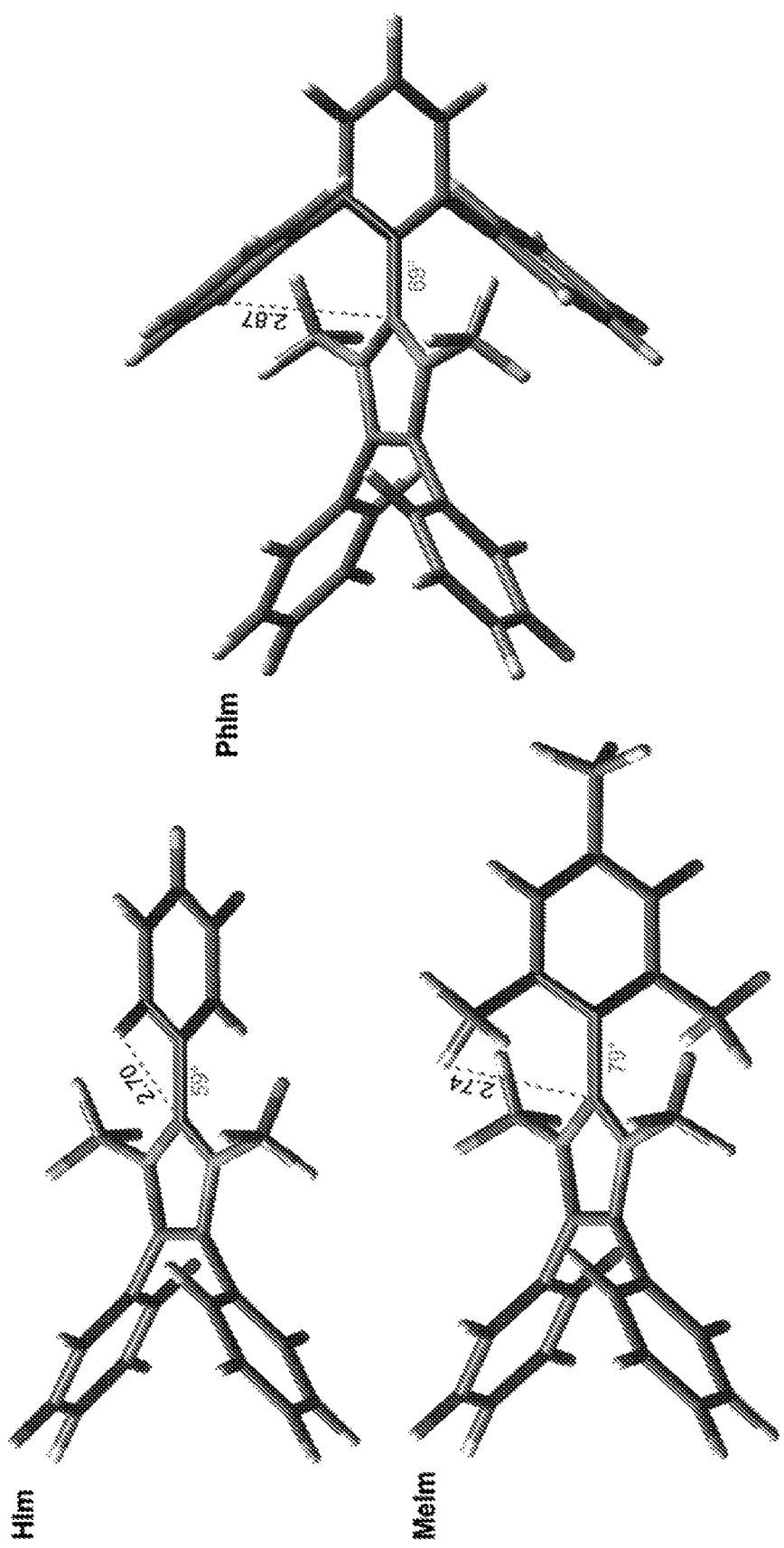
FIG. 9 shows solution dihedral angles of embodiments of small molecule imidazolium compounds. Specifically, the structures shown of HIm, MeIm, and PhIm were optimized using B3LYP DFT calculations at 298.15 K in water. The distance (Å) from the C2-position to the closest atom of the adjacent steric protecting group and the dihedral angle between the imidazolium plane and the phenyl substituent in C2 position are labeled.

In order to explain the differences in stability between the chemical structures studied, density-functional theory (DFT) was used to determine the free energy of states along two degradation pathways: de-methylation and ring-opening (FIG. 4A) according to protocols reported by Long, H.; Pivovar, B. *J Phys. Chem. C* 2014, 118, 9880, incorporated herein by reference in its entirety. The computed free energies for degradation via de-methylation ($\Delta G^{\ddagger}_{SN2}$) of HIm (27.1 kcal mol$^{-1}$), MeIm (26.9 kcal mol$^{-1}$), and PhIm (27.3 kcal mol$^{-1}$) are very similar (see FIG. 7 for structures), which indicates that the o-methyl steric protecting groups have no effect on the rate of de-methylation. In contrast, the free energy of the first transition state for ring-opening degradation ($\Delta G^{\ddagger}_{C2}$, see FIG. 8 for structure), which involves the addition of OH$^-$ at the C2-position to form $IS_{C2}$, increases from 14.6 kcal mol$^{-1}$ (HIm) to 27.7 kcal mol$^{-1}$ (MeIm), and to 30.2 kcal mol$^{-1}$ (PhIm). The mechanism of degradation is dependent on the difference in free energy of activation between $TS_{SN2}$ and $TS_{C2}$. For example, $TS_{C2}$ for HIm is 12.5 kcal mol$^{-1}$ lower than $\Delta G^{\ddagger}_{SN2}$, suggesting that degradation via ring-opening is the degradation pathway. Conversely, $\Delta G^{\ddagger}_{C2}$ of MeIm and PhIm are both larger than $\Delta G^{\ddagger}_{SN2}$, suggesting de-methylation to be the main degradation mechanism. The change in degradation mechanism is a result of sterically-protecting the C2-position, and agrees well with the experimental data. Additionally, the calculated structures of MeIm and PhIm reveal larger dihedral angles between the imidazolium plane and the C2-attached phenyl than that observed for HIm (FIG. 9); the dihedral angle increased from 59° for HIm to 79° for MeIm to 69° for PhIm. The dihedral angles appear related to the molecular stability. Despite HIm demonstrating the lowest stability of three model compounds tested in this work, HIm showed high stability relative to other 2-phenylimidazoliums reported in the literature ($t_{1/2}$ 1370 h in 3 M NaOD at 80° C.). 1,3-dimethyl-2-phenylimidazolium (possessing a dihedral angle of 57°) was found to exhibit a $t_{1/2}$ of 107 h under milder alkaline conditions of 1 M NaOH at 80° C. See, Price, S. C., Williams, K. S.; Beyer, F. L. *ACS Macro Lett.* 2014, 3, 160, herein incorporated by reference in its entirety. 3-ethyl-1-methyl-2-phenylimidazolium degraded by 26% after 168 h in 2 M $KOH_{aq}$ at 80° C. See, Lin, B.; Dong, H.; Li, Y.; Si, Z.; Gu, F.; Yan, F. *Chem. Mater.* 2013, 25, 1858, herein incorporated by reference in its entirety. As such, the improvement in stability is confirmed to be attributed to the 4,5-diphenyl substituents of HIm. Additionally, the single crystal XRD structure of MeIm, in its iodide form (FIG. 4B), revealed that one of the solid-state dihedral angles was 90°, rendering the methyl-groups that flank the C2-position as effective C2-protecting groups. HMT-PMPI possesses the same sterically-hindering groups that are proximal to the C2-position and the mesitylene group, which is expected to possess the 90° angle with respect to the imidazolium group, and which explains the stability of this anion exchange polymer in aggressively caustic conditions.

Figure 10:
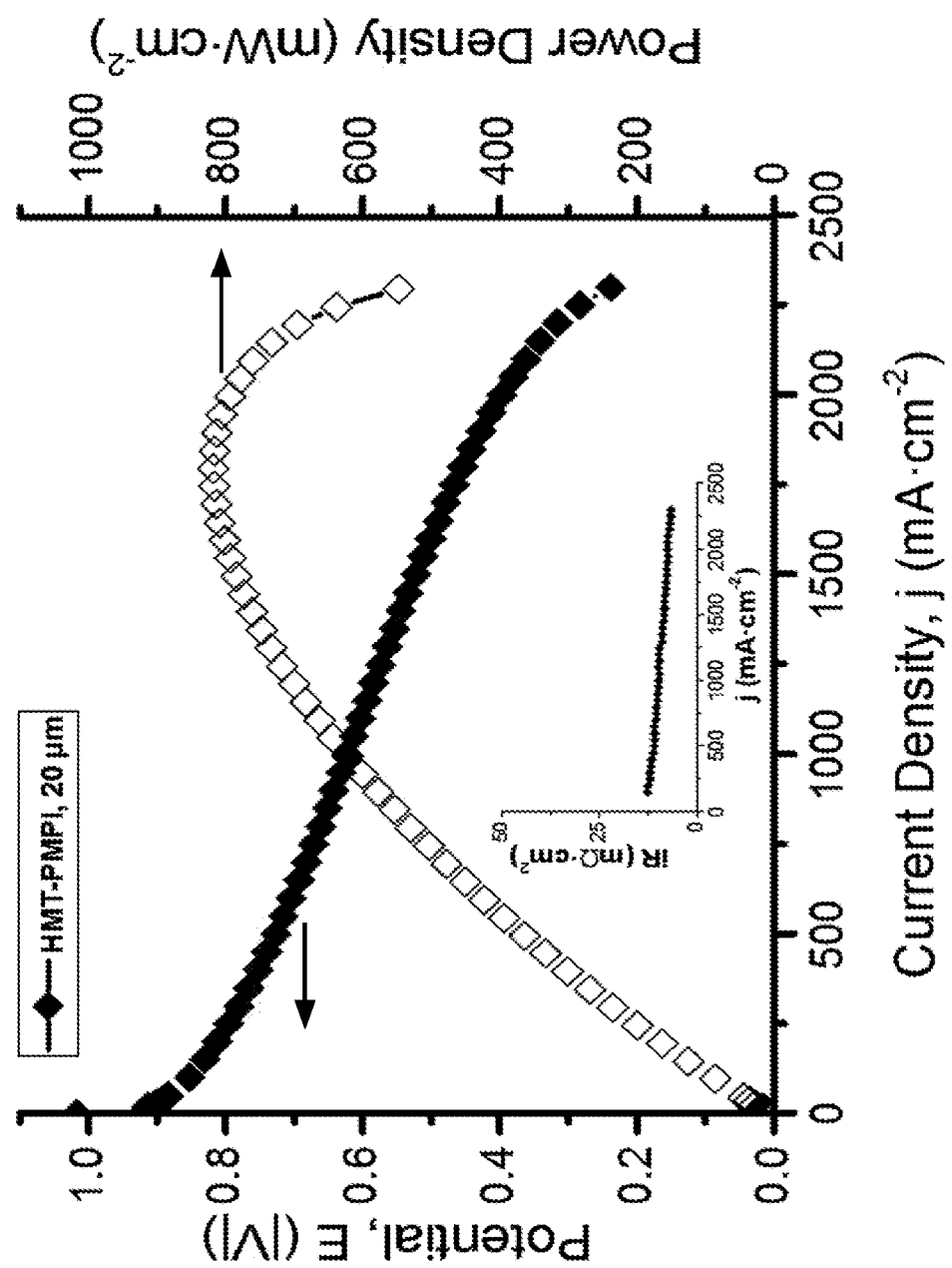
FIG. 10 is a graph of polarization and related power density data of an embodiment of a polymer of the present disclosure (HMT-PMPI), specifically a Beginning of Life (BOL) HMT-PMPI-based AEMFC with 0.5/0.5 mg Pt·cm$^{-2}$ at the anode/cathode and 20 μm total membrane thickness. Testing conditions were 80° C., 0.25/0.5 slpm $H_2/O_2$, with zero backpressure.

The hydration level of OH$^-$ has a critical effect on the stability of the cationic group, suggesting that currently employed aqueous-based alkali ex-situ methods used to measure alkaline stability of cationic groups may underestimate the stability of cations in the specific case of fuel cell applications, but this assertion does not apply to other applications, e.g. alkaline membrane electrolyzers, metal-air batteries, or electrodialysis, in which exposure of the cationic membrane to caustic liquids is maintained. An alkaline exchange membrane fuel cell (AEMFC) with 0.5/0.5 mg Pt·cm$^{-2}$ and membrane thickness of 20 μm operated at 80° C. attained a power density of 818 mW at a current density of 1.8 A·cm$^{-2}$, under zero backpressure (FIG. 10). Conditions at the anode/cathode were 0.5/0.25 slpm $H_2/O_2$ and 70%/100% RH. This is among the highest power densities achieved in AEMFCs under zero backpressure. Moreover, the in-situ hydroxide conductivity estimated from the high frequency resistance was 280±80 mS·cm, which is more than an order of magnitude greater than the ex-situ conductivity measurement. The performance of the AEMFC diminished over a period of 10 h total operation, because of excessive swelling of the membrane and its partial dissolution at these temperatures, consistent with the observation that fully methylated HMT-PMPI dissolved in water at 100° C.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A polymer comprising a repeating unit of Formula (I):

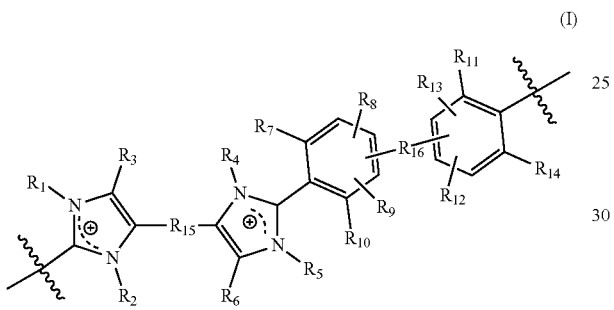

(I)

wherein:
$R_1$, $R_2$, $R_4$, and $R_5$ are each independently selected from absent, alkyl, perfluoroalkyl, heteroalkyl, aryl, and aralkyl;
provided that
at least one of $R_1$ and $R_2$ is selected from alkyl, perfluoroalkyl, heteroalkyl, aryl, and aralkyl,
when one of $R_1$ and $R_2$ is absent, the imidazolyl group to which the absent $R_1$ or $R_2$ is connected is neutral; and
at least one of $R_4$ and $R_5$ is selected from alkyl, perfluoroalkyl, heteroalkyl, aryl, and aralkyl; and
when one of $R_4$ and $R_5$ is absent, the imidazolyl group to which the absent $R_4$ or $R_5$ is connected is neutral;
$R_3$ and $R_6$ are each independently selected from alkyl, perfluoroalkyl, heteroalkyl, aryl, aralkyl, and heteroaryl;
$R_{15}$ is arylene optionally substituted with 1, 2, 3, or 4 substituents independently selected from alkyl, perfluoroalkyl, heteroalkyl, and halo;
$R_{16}$ is arylene optionally substituted with 1, 2, 3, or 4 substituents independently selected from alkyl, perfluoroalkyl, heteroalkyl, and halo;
$R_7$, $R_{10}$, $R_{11}$, and $R_{14}$ are each independently selected from alkyl, perfluoroalkyl, and heteroalkyl; and
$R_8$, $R_9$, $R_{12}$, and $R_{13}$ are each independently selected from hydrogen, alkyl, perfluoroalkyl, and heteroalkyl.

2. The polymer of claim 1, wherein the polymer comprises a repeating unit of Formula (I-A):

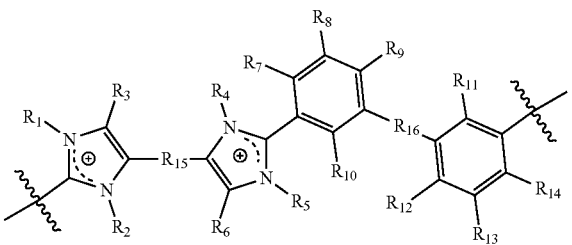

(I-A)

wherein:
$R_1$, $R_2$, $R_4$, and $R_5$ are each independently selected from absent, alkyl, perfluoroalkyl, heteroalkyl, aryl, and aralkyl;
provided that
at least one of $R_1$ and $R_2$ is selected from alkyl, perfluoroalkyl, heteroalkyl, aryl, and aralkyl,
when one of $R_1$ and $R_2$ is absent, the imidazolyl group to which the absent $R_1$ or $R_2$ is connected is neutral;
at least one of $R_4$ and $R_5$ is selected from alkyl, perfluoroalkyl, heteroalkyl, aryl, and aralkyl; and
when one of $R_4$ and $R_5$ is absent, the imidazolyl group to which the absent $R_4$ or $R_5$ is connected is neutral;
$R_3$ and $R_6$ are each independently selected from alkyl, perfluoroalkyl, heteroalkyl, aryl, aralkyl, and heteroaryl;
$R_{15}$ is arylene optionally substituted with 1, 2, 3, or 4 substituents independently selected from alkyl, perfluoroalkyl, heteroalkyl, and halo;
$R_{16}$ is arylene optionally substituted with 1, 2, 3, or 4 substituents independently selected from alkyl, perfluoroalkyl, heteroalkyl, and halo;
$R_7$, $R_{10}$, $R_{11}$, and $R_{14}$ are each independently selected from alkyl, perfluoroalkyl, and heteroalkyl; and
$R_8$, $R_9$, $R_{12}$, and $R_{13}$ are each independently selected from hydrogen, alkyl, perfluoroalkyl, and heteroalkyl.

3. The polymer of claim 1, wherein the polymer comprises a repeating unit of Formula (I-B):

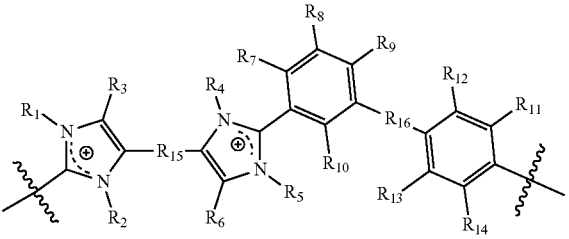

(I-B)

wherein:
$R_1$, $R_2$, $R_4$, and $R_5$ are each independently selected from absent, alkyl, perfluoroalkyl, heteroalkyl, aryl, and aralkyl;
provided that
at least one of $R_1$ and $R_2$ is selected from alkyl, perfluoroalkyl, heteroalkyl, aryl, and aralkyl,
when one of $R_1$ and $R_2$ is absent, the imidazolyl group to which the absent $R_1$ or $R_2$ is connected is neutral; and
at least one of $R_4$ and $R_5$ is selected from alkyl, perfluoroalkyl, heteroalkyl, aryl, and aralkyl; and when one of $R_4$ and $R_5$ is absent, the imidazolyl group to which the absent $R_4$ or $R_5$ is connected is neutral;

$R_3$ and $R_6$ are each independently selected from alkyl, perfluoroalkyl, heteroalkyl, aryl, aralkyl, and heteroaryl;

$R_{15}$ is arylene optionally substituted with 1, 2, 3, or 4 substituents independently selected from alkyl, perfluoroalkyl, heteroalkyl, and halo;

$R_{16}$ is arylene optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen, alkyl, perfluoroalkyl, and heteroalkyl.

4. The polymer of claim 1, wherein the polymer comprises a repeating unit of Formula (I-C):

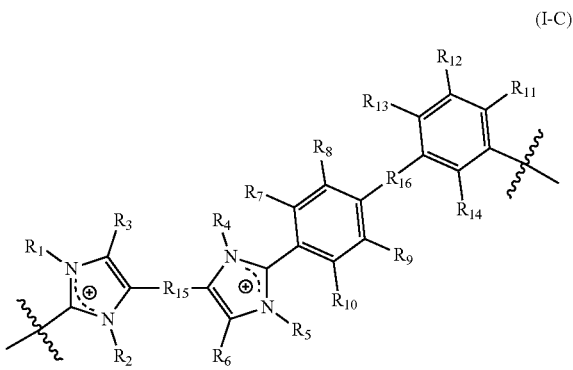

(I-C)

wherein:

$R_1$, $R_2$, $R_4$, and $R_5$ are each independently selected from absent, alkyl, perfluoroalkyl, heteroalkyl, aryl, and aralkyl;

provided that
at least one of $R_1$ and $R_2$ is selected from alkyl, perfluoroalkyl, heteroalkyl, aryl, and aralkyl,
when one of $R_1$ and $R_2$ is absent, the imidazolyl group to which the absent $R_1$ and $R_2$ is connected is neutral; and
at least one of $R_4$ and $R_5$ is selected from alkyl, perfluoroalkyl, heteroalkyl, aryl, and aralkyl; and
when one of $R_4$ and $R_5$ is absent, the imidazolyl group to which the absent $R_4$ or $R_5$ is connected is neutral;

$R_3$ and $R_6$ are each independently selected from alkyl, perfluoroalkyl, heteroalkyl, aryl, aralkyl, and heteroaryl;

$R_{15}$ is arylene optionally substituted with 1, 2, 3, or 4 substituents independently selected from alkyl, perfluoroalkyl, heteroalkyl, and halo;

$R_{16}$ is arylene optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen, alkyl, perfluoroalkyl, and heteroalkyl.

5. The polymer of claim 1, wherein the polymer comprises a repeating unit of Formula (I-D):

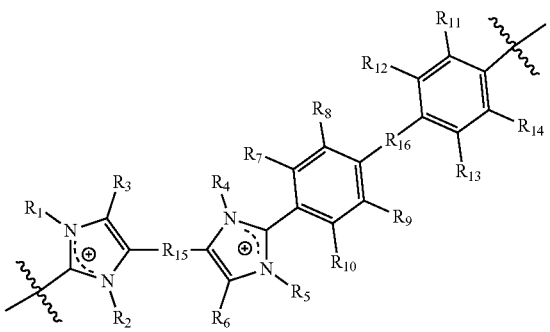

(I-D)

wherein:

$R_1$, $R_2$, $R_4$, and $R_5$ are each independently selected from absent, alkyl, perfluoroalkyl, heteroalkyl, aryl, and aralkyl;

provided that
at least one of $R_1$ and $R_2$ is selected from alkyl, perfluoroalkyl, heteroalkyl, aryl, and aralkyl,
when one of $R_1$ and $R_2$ is absent, the imidazolyl group to which the absent $R_1$ or $R_2$ is connected is neutral; and
at least one of $R_4$ and $R_5$ is selected from alkyl, perfluoroalkyl, heteroalkyl, aryl, and aralkyl; and
when one of $R_4$ and $R_5$ is absent, the imidazolyl group to which the absent $R_4$ or $R_5$ is connected is neutral;

$R_3$ and $R_6$ are each independently selected from alkyl, perfluoroalkyl, heteroalkyl, aryl, aralkyl, and heteroaryl;

$R_{15}$ is arylene optionally substituted with 1, 2, 3, or 4 substituents independently selected from alkyl, perfluoroalkyl, heteroalkyl, and halo;

$R_{16}$ is arylene optionally substituted with 1, 2, 3, or 4 substituents independently selected from alkyl, perfluoroalkyl, heteroalkyl, and halo;

$R_7$, $R_{10}$, $R_{11}$, and $R_{14}$ are each independently selected from alkyl, perfluoroalkyl, and heteroalkyl; and $R_8$, $R_9$, $R_{12}$, and $R_{13}$ are each independently selected from hydrogen, alkyl, perfluoroalkyl, and heteroalkyl.

6. The polymer of claim 1, wherein $R_1$, $R_2$, $R_4$, and $R_5$ are each independently selected from absent, methyl, and trifluoromethyl; provided that
at least one of $R_1$ and $R_2$ is selected from methyl and trifluoromethyl; and
at least one of $R_4$ and $R_5$ is selected from methyl and trifluoromethyl.

7. The polymer of claim 1, wherein $R_3$ and $R_6$ are each independently aryl.

8. The polymer of claim 1, wherein $R_3$ and $R_6$ are each independently methyl.

9. The polymer of claim 1, wherein $R_{15}$ and $R_{16}$ are each independently arylene, optionally substituted with 1, 2, 3, or 4 substituents independently selected from alkyl and halo.

10. The polymer of claim 1, wherein $R_7$, $R_{10}$, $R_{11}$, and $R_{14}$ are each independently alkyl.

11. The polymer of claim 1, further comprising one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis (3,5-bis(trifluoromethyl)phenyl)borate, bis(trifluoromethane)sulfonamide, and any combination thereof, wherein the one or more anions $X^-$ counterbalance one or more positive charges in the polymer.

12. A polymer comprising a repeating unit of Formula (II):

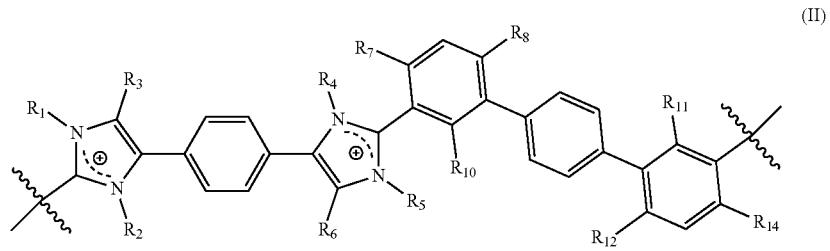

(II)

wherein:
$R_1$, $R_2$, $R_4$, and $R_5$ are each independently selected from absent, alkyl, perfluoroalkyl, heteroalkyl, aryl, and aralkyl;
provided that
at least one of $R_1$ and $R_2$ is selected from alkyl, perfluoroalkyl, heteroalkyl, aryl, and aralkyl,
when one of $R_1$ and $R_2$ is absent, the imidazolyl group to which the absent $R_1$ or $R_2$ is connected is neutral; and
at least one of $R_4$ and $R_5$ is selected from alkyl, perfluoroalkyl, heteroalkyl, aryl, and aralkyl; and
when one of $R_4$ and $R_5$ is absent, the imidazolyl group to which the absent $R_4$ or $R_5$ is connected is neutral;
$R_3$ and $R_6$ are each independently selected from alkyl, perfluoroalkyl, heteroalkyl, aryl, aralkyl, and heteroaryl;
$R_7$, $R_{10}$, $R_{11}$, and $R_{14}$ are each independently selected from alkyl, perfluoroalkyl, and heteroalkyl; and
$R_8$ and $R_{12}$ are each independently selected from hydrogen, alkyl, perfluoroalkyl, and heteroalkyl.

13. The polymer of claim 12, wherein $R_1$, $R_2$, $R_4$, and $R_5$ are each independently selected from absent, methyl, and trifluoromethyl;

provided that
at least one of $R_1$ and $R_2$ is selected from methyl and trifluoromethyl, and
at least one of $R_4$ and $R_5$ is selected from methyl and trifluoromethyl.

14. The polymer of claim 12, wherein $R_3$ and $R_6$ are each independently phenyl.

15. The polymer of claim 12, wherein $R_3$ and $R_6$ are each independently methyl.

16. The polymer of claim 12, wherein $R_7$, $R_8$, $R_{10}$, $R_{11}$, $R_{12}$, and $R_{14}$ are each independently methyl.

17. The polymer of claim 12, further comprising one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis (3,5-bis(trifluoromethyl)phenyl)borate, bis(trifluoromethane)sulfonamide, and any combination thereof, wherein the one or more anions $X^-$ counterbalance one or more positive charges in the polymer.

18. A random polymer, comprising repeating units of Formula (IV-A), (IV-B), and (IV-C):

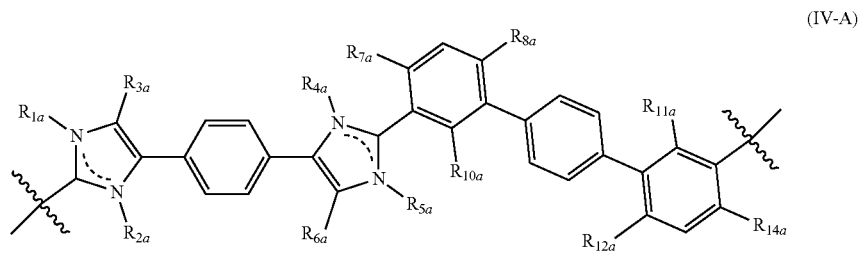

(IV-A)

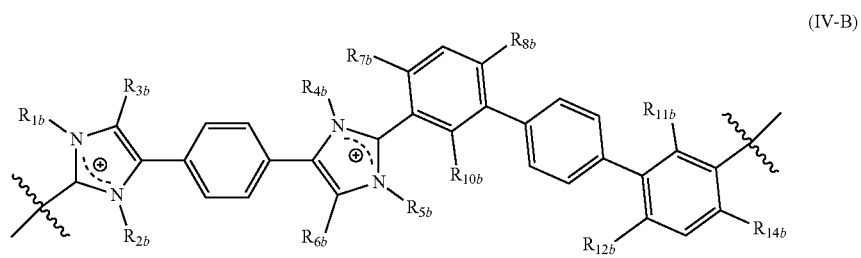

(IV-B)

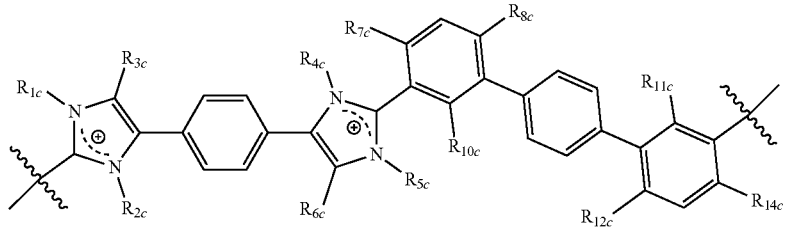

(IV-C)

wherein

- one of $R_{1a}$ and $R_{2a}$ is absent and the remaining $R_{1a}$ or $R_{2a}$ is selected from alkyl, perfluoroalkyl, heteroalkyl, aryl, and aralkyl;
- one of $R_{4a}$ and $R_{5a}$ is absent and the remaining $R_{4a}$ or $R_{5a}$ is selected from alkyl, perfluoroalkyl, heteroalkyl, aryl, and aralkyl;
- one of $R_{1b}$, $R_{2b}$, $R_{4b}$, and $R_{5b}$ is absent and the imidazolyl group to which the absent $R_{1b}$, $R_{2b}$, $R_{4b}$, or $R_{5b}$ is connected is neutral, and the remaining three of $R_{1b}$, $R_{2b}$, $R_{4b}$, and $R_{5b}$ are each independently selected from alkyl, perfluoroalkyl, heteroalkyl, aryl, and aralkyl;
- $R_{1c}$, $R_{2c}$, $R_{4c}$, and $R_{5c}$ are each independently selected from alkyl, perfluoroalkyl, heteroalkyl, aryl, and aralkyl;
- $R_{3a}$, $R_{6a}$, $R_{3b}$, $R_{6b}$, $R_{3c}$, and $R_{6c}$ are each independently selected from alkyl, perfluoroalkyl, heteroalkyl, aryl, aralkyl, and heteroaryl;
- $R_{7a}$, $R_{10a}$, $R_{11a}$, $R_{14a}$, $R_{7b}$, $R_{10b}$, $R_{11b}$, $R_{14b}$, $R_{7c}$, $R_{10c}$, $R_{11c}$, and $R_{14c}$ are each independently selected from alkyl, perfluoroalkyl, and heteroalkyl; and
- $R_{8a}$, $R_{12a}$, $R_{8b}$, $R_{12b}$, $R_{8c}$, and $R_{12c}$ are each independently selected from hydrogen, alkyl, perfluoroalkyl, and heteroalkyl;
- wherein the polymer comprises m mole percentage repeating units of Formula (IV-A), n mole percentage repeating units of Formula (IV-B), and p mole percentage repeating units of Formula (IV-C), and
  m is from 0 mole percent to 60 mole percent,
  n+p is 40 mole percent to 100 mole percent, and
  $m+n+p=100\%$.

19. An ionic membrane comprising a polymer of claim 1.

20. An ionomer comprising a polymer of claim 1, wherein the ionomer is optionally incorporated into a catalyst layer of a fuel cell, of an electrolyzer, or of other electrochemical device.

* * * * *